(12) United States Patent
Gilbert et al.

(10) Patent No.: US 7,472,463 B2
(45) Date of Patent: *Jan. 6, 2009

(54) PROCESS FOR PRODUCING A STABILIZED COMPRESSED TAMPON

(75) Inventors: Steven Ray Gilbert, Fairfield, OH (US);
Matthew Howard Wasson, Cincinnati, OH (US); Edward Paul Carlin, Deerfield Township, OH (US); Margaret Henderson Hasse, Wyoming, OH (US); Dale Francis Bittner, Crosby Township, OH (US); Douglas Toms, Sycamore Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/809,691

(22) Filed: Jun. 1, 2007

(65) Prior Publication Data

US 2007/0234532 A1    Oct. 11, 2007

Related U.S. Application Data

(63) Continuation-in-part of application No. 10/887,645, filed on Jul. 9, 2004, which is a continuation-in-part of application No. 10/717,269, filed on Nov. 19, 2003, now Pat. No. 7,120,977, which is a continuation-in-part of application No. 10/435,822, filed on May 12, 2003, now Pat. No. 7,124,483.

(51) Int. Cl.
*A61F 13/20* (2006.01)

(52) U.S. Cl. .......................................................... 28/118

(58) Field of Classification Search .................... 28/118, 28/119, 120, 116, 122, 121, 123, 165, 282, 28/283; 604/904, 385.17, 385.18, 379, 380, 604/286; 264/413, 443, 479, 489, 486, 319, 264/345, 402–405, 294, 320, 325, 327; 156/62.2, 156/180, 166, 167, 285, 311
See application file for complete search history.

(56) References Cited

U.S. PATENT DOCUMENTS

| | | | | | |
|---|---|---|---|---|---|
| 2,077,231 | A | * | 4/1937 | Fourness et al. | 28/118 |
| 2,976,579 | A | * | 3/1961 | Rabell | 28/119 |
| 3,095,343 | A | * | 6/1963 | Berger | 156/180 |
| 3,431,909 | A | | 3/1969 | Krusko | |
| 3,610,243 | A | | 10/1971 | Jones, Sr. | |
| 3,643,661 | A | | 2/1972 | Crockford | |
| 3,658,626 | A | * | 4/1972 | Berger et al. | 156/441 |

(Continued)

OTHER PUBLICATIONS

PCT International Search Report dated Dec. 13, 2005.

(Continued)

*Primary Examiner*—Amy B Vanatta
(74) *Attorney, Agent, or Firm*—James E. Oehlenschlager; Jason J. Camp; David M. Weirich

(57) ABSTRACT

A process and apparatus for producing compressed, gas-stabilized tampons are disclosed. The gas-stabilized tampons include tampons having preferably multiple folds for improved leakage protection and comfort through improved expansion characteristics. The number of folds can vary from 3 to 20 and greater. The process includes the step of forcing a gas through the compressed tampon. The gas can include steam.

18 Claims, 23 Drawing Sheets

U.S. PATENT DOCUMENTS

| | | | |
|---|---|---|---|
| 3,674,025 A * | 7/1972 | Bleuer | 604/12 |
| 3,819,435 A * | 6/1974 | Roberts et al. | 156/62.2 |
| 3,874,032 A * | 4/1975 | Simon et al. | 28/119 |
| 3,971,378 A | 7/1976 | Krantz | |
| 3,995,636 A * | 12/1976 | Murray et al. | 604/286 |
| 4,081,884 A * | 4/1978 | Johst et al. | 28/119 |
| 4,326,527 A * | 4/1982 | Wollangk et al. | 604/371 |
| 4,627,849 A | 12/1986 | Walton | |
| 5,084,038 A * | 1/1992 | Sheldon et al. | 604/358 |
| 5,153,971 A * | 10/1992 | Van Iten | 28/118 |
| 5,161,283 A * | 11/1992 | Hansen | 19/148 |
| 5,382,153 A * | 1/1995 | Nettelnstroth | 425/308 |
| 6,003,216 A * | 12/1999 | Hull et al. | 28/119 |
| 6,283,952 B1 * | 9/2001 | Child et al. | 604/540 |
| 6,554,814 B1 | 4/2003 | Agyapong | |
| 6,682,513 B2 | 1/2004 | Agyapong | |
| 6,719,743 B1 | 4/2004 | Wada | |
| 6,740,070 B2 | 5/2004 | Agyapong | |
| 2001/0009711 A1 * | 7/2001 | Latimer et al. | 428/182 |
| 2003/0172504 A1 | 9/2003 | Sageser et al. | |
| 2003/0233742 A1 * | 12/2003 | Jones et al. | 28/118 |
| 2004/0226152 A1 | 11/2004 | Prosise et al. | |
| 2004/0244165 A1 | 12/2004 | Bittner et al. | |
| 2005/0027275 A1 | 2/2005 | Wasson et al. | |
| 2005/0096619 A1 * | 5/2005 | Costa | 604/385.17 |
| 2005/0096621 A1 * | 5/2005 | Almond | 604/385.18 |

OTHER PUBLICATIONS

U.S. Appl. No. 10/887,645, filed Jul. 9, 2004, Matthew Howard Wasson.

* cited by examiner

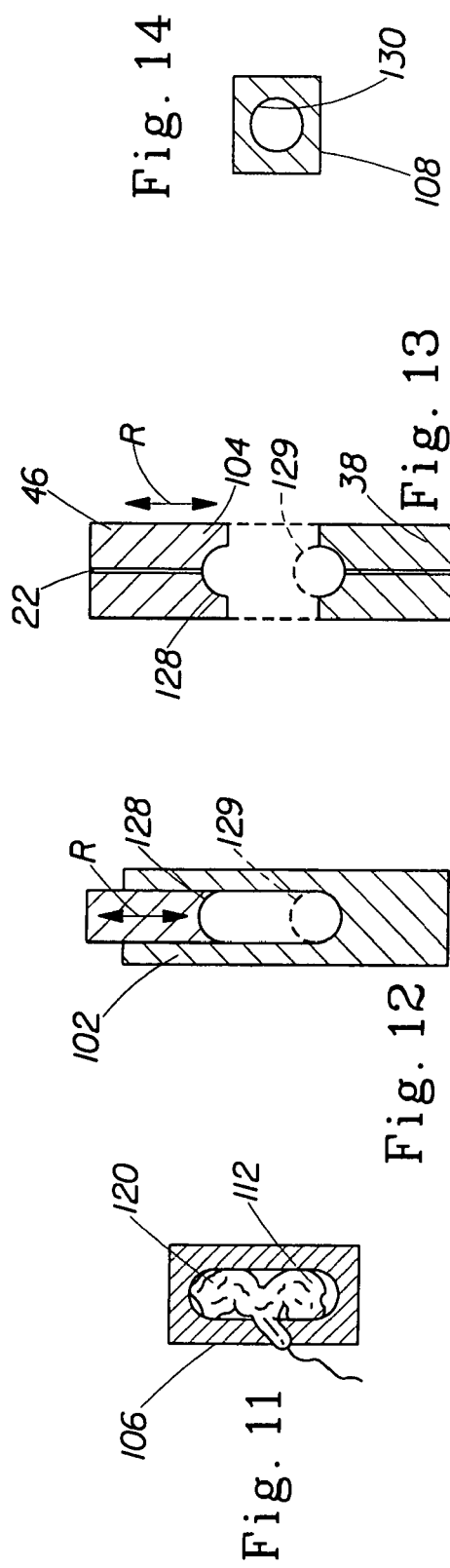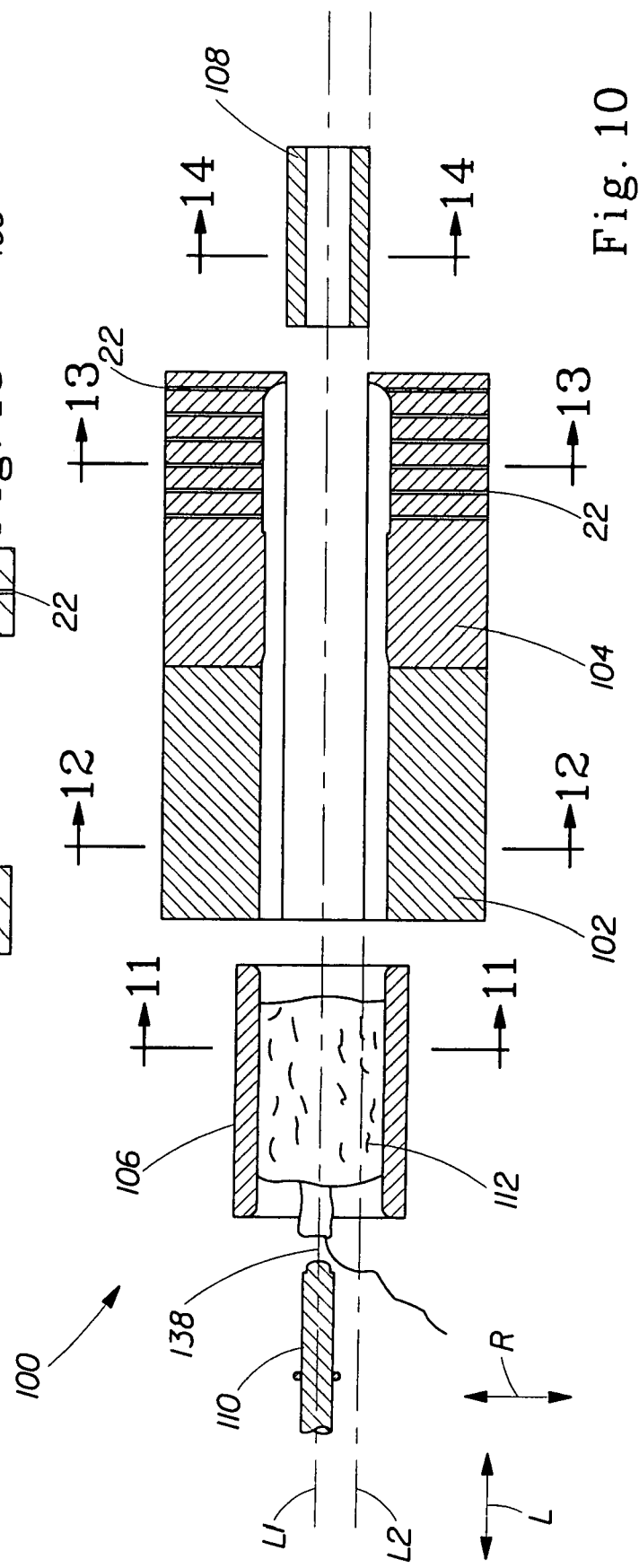

PROCESS FOR PRODUCING A STABILIZED COMPRESSED TAMPON

CROSS REFERENCE TO RELATED APPLICATIONS

This application is a continuation application of U.S. application Ser. No. 10/887,645 filed on Jul. 9, 2004, which is a continuation-in-part of U.S. application Ser. No. 10/717,269, filed on Nov. 19, 2003 now U.S. Pat. No. 7,120,977, which is a continuation-in-part of U.S. application Ser. No. 10/435,822, filed on May 12, 2003 now U.S. Pat. No. 7,124,483.

FIELD OF THE INVENTION

This invention relates to catamenial tampons. More particularly, the invention relates to a compressed, gas-stabilized tampon.

BACKGROUND OF THE INVENTION

It is well known in the art, that during the production of tampons, tampon pledgets have a tendency to re-expand to their original dimensions after a compression step. Heat setting has been utilized to overcome this tendency. Heat setting is the application of heat to a compressed tampon pledget designed to "set" or stabilize the tampon in the compressed state. Currently, tampons are set or stabilized by either conductive heating or microwave heating, both of which have drawbacks.

Commonly, conductive heating methods do not uniformly stabilize the tampon and may result in the alteration of absorbent qualities in the outer layer of the tampon because the dense, compacted material on the outside of the tampon dries more quickly than the inside. Conductive heating methods may also be time intensive because the air inside the tampon must be heated to dry the fibers via conduction from outside the pledget to the inside. As well, high temperatures that may decrease cycle times cannot be utilized in conductive heating methods because these temperatures may be above the melting point of tampon overwraps resulting in a melted product.

While microwave heating can be a faster method of stabilizing tampons than conductive heating, microwave heating does not uniformly stabilize tampons and may create "hot spots" within the tampon and may also melt the overwrap of the tampon. As well, only a small fraction of the outputted energy in microwave heating actually goes into stabilizing the tampon, thus energy costs of this method are relatively high.

The present invention addresses the problems associated with both the conductive heating and the microwave heating by providing a time-efficient process for uniformly stabilizing a compressed tampon pledget by forcing a gas through the compressed tampon pledget. Furthermore, the process of the present invention has the benefit of more consistent stabilization while at the same time being less dependent on incoming moisture.

The present invention is also directed to a gas-stabilized tampon having multiple folds for improved leakage protection and comfort through improved expansion characteristics.

SUMMARY OF THE INVENTION

A process for producing a stabilized compressed tampon is provided. The process comprises the steps of providing a tampon pledget, providing a mold, wherein the mold contains a plurality of pores. The process further comprises the steps of compressing the tampon pledget in the mold to form a compressed tampon pledget, and stabilizing the compressed tampon pledget by forcing a gas through the pores while the compressed tampon is maintained in compression by the mold.

In certain embodiments the amount of said pores per unit area varies along the length of said mold.

In certain embodiments the mold is a split cavity mold comprising an inner cavity defined by an inner surface formed from a first split cavity mold member and a second split cavity mold member wherein said first split cavity mold member has a first and second end that corresponds to a first and second end of said second split cavity mold member. In certain embodiments the amount of said pores per unit area in said inner surface increases along the length of the split cavity mold in the direction of the first end of the first and second split cavity mold members or in certain other embodiments the amount of said pores per unit area in said inner surface increases along the length of the split cavity mold in the direction of the second end of the first and second split cavity mold members.

In certain embodiments the mold is a unitary mold comprising an inner cavity defined by an inner surface, an open proximal end and a closed distal end. In certain embodiments the amount of said pores per unit area in said inner surface increases along the length of the unitary mold in the direction of the proximal end of the inner cavity or in certain other embodiments the amount of said pores per unit area in said inner surface increases along the length of the unitary mold in the direction of the distal end of the inner cavity.

Another process for producing a stabilized compressed tampon is provided. The process comprises the steps of providing a tampon pledget, providing a mold, the mold containing a plurality of pores, wherein the pores vary in size from about macroscopic to about submicroscopic. The process further comprises the steps of compressing the tampon pledget into the mold to form a compressed tampon pledget, and stabilizing the compressed tampon pledget by forcing a gas through the pores while the compressed tampon pledget is maintained in compression by the mold.

In certain embodiments the size of said pores varies along the length of said mold.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying Figures, in which:

FIG. 10 is a simplified longitudinal cross-sectional view of one embodiment of the process of the present invention, particularly suitable for mass-production of stabilized tampons, including two split molds—a compression mold and a stabilization mold—that are both shown in their open positions and aligned with a pledget infeed carrier and a tampon discharge carrier.

FIG. 11 is a simplified radial cross-sectional view of a pledget infeed carrier of FIG. 10, taken along line 11-11.

FIG. 12 is a simplified radial cross-sectional view of the split compression mold of FIG. 10, taken along line 12-12.

FIG. 13 is a simplified radial cross-sectional view of the split stabilization mold of FIG. 10, taken along line 13-13.

FIG. 14 is a simplified radial cross-sectional view of a tampon discharge carrier of FIG. 10, taken along line 14-14.

DETAILED DESCRIPTION OF THE INVENTION

As used herein, "compression" refers to the process of pressing, squeezing, compacting or otherwise manipulating the size, shape, and/or volume of a material to obtain a tampon having a vaginally insertable shape. The term "compressed" refers to the state of a material or materials subsequent to compression. Conversely, the term "uncompressed" refers to the state of a material or materials prior to compression. The term "compressible" is the ability of a material to undergo compression.

The term "joined" or "attached," as used herein, encompasses configurations in which a first element is directly secured to a second element by affixing the first element directly to the second element; configurations in which the first element is indirectly secured to the second element by affixing the first element to intermediate member(s) which in turn are affixed to the second element; and configurations in which the first element is integral with the second element; i.e., the first element is essentially part of the second element.

Figure 1:
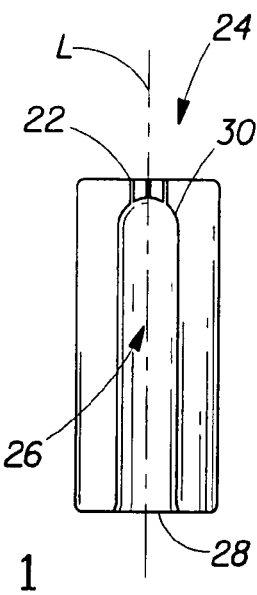
FIG. 1 is a cross section of a unitary embodiment of the permeable mold with pores located axially along the mold.
Figure 2:
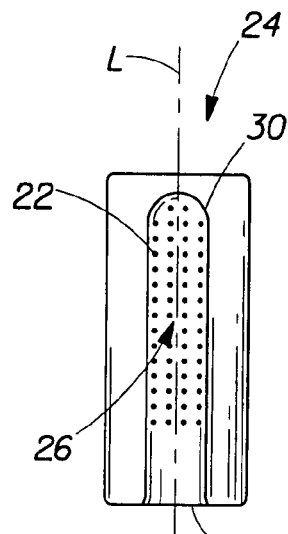
FIG. 2 is a cross section of a unitary embodiment of the permeable mold with pores located radially along the mold.

As used herein, "mold" refers to a structure for shaping a tampon pledget during compression and/or retaining the shape for a compressed tampon pledget subsequent to compression during the stabilization process. Molds have an inner surface defining an inner cavity and an outer surface. The inner cavity is structured to define or mirror the shape of the compressed absorbent tampon pledget. Thus, in some embodiments the tampon pledget conforms to the shape of the inner cavity of the mold by a restraining force to result in a self-sustaining shape and is retained in the inner cavity during the stabilization process. In other embodiments, the mold retains the shape of the compressed tampon pledget during the stabilization process. The inner cavity may be profiled to achieve any shape known in the art including, but not limited to, cylindrical, rectangular, triangular, trapezoidal, semi-circular, hourglass, serpentine or other suitable shapes. The outer surface of the mold is the surface external to the inner surface and can be profiled or shaped in any manner, such as, rectangular, cylindrical or oblong. The mold may comprise one or more members. One mold used in the present invention may be a unitary mold, comprising one member, as shown in FIGS. 1 and 2, or "split cavity mold" as shown in FIG. 3, FIG. 4, FIG. 5, FIG. 6, and FIG. 7. Split cavity molds may be preferred when producing shaped tampons, such as those disclosed in U.S. patent application Ser. No. 10/150,050 entitled "Substantially Serpentine Shaped Tampon," and U.S. patent application Ser. No. 10/150,055, entitled "Shaped Tampon," both filed on Mar. 18, 2002. Whereas unitary molds may be used for less complex shapes such as cylindrical or substantial cylindrical.

The term "permeable," as used herein, refers to the ability of a material to allow the spread or infusion of a gas through the material's composition. A material may be permeable due to its composition or the material, may be fabricated from impermeable material then modified to become permeable, either chemically, mechanically, or electrically, such as, for example by acid etching, drilling, or aperturing.

As used herein the terms "pledget" or "tampon pledget" are intended to be interchangeable and refer to a construction of absorbent material prior to the compression of such construction into a tampon.

The term "pores," as used herein, refers to small openings or interstices that connect the inner surface of the mold with the outer surface of the mold admitting the passage and infusion of gases into and through a compressed tampon pledget contained within the inner cavity of the mold.

As used herein, "self-sustaining" is a measure of the degree or sufficiency to which the tampon retains its compressed form after stabilization such that in the subsequent to the absence of external forces, the resulting tampon will tend to retain its vaginally insertable shape and size. For tampons, it is found that control of the level of moisture within the tampon is a factor for helping the tampon to retain its shape subsequent the absence of the external compression forces. It will be understood by one of skill in the art that this self-sustaining form need not, and preferably does not persist during actual use of the tampon. That is, once the tampon is inserted into the vagina or other body cavity and begins to acquire fluid, the tampon will begin to expand and may lose its self-sustaining form.

The term "shaped tampons," as used herein, refers to compressed tampon pledgets having either a substantially serpentine shape, a "undercut" or "waist". The phrase "substantially serpentine" refers to a non-linear dimension between any two points spaced at least about 5 mm apart. The term "undercut" refers to tampons having a protuberance or indentation that impedes the withdrawal from a unitary mold. For example, shaped tampons may be hourglass shaped having at least one perimeter in the center of the tampon or "waist" that is less than both an insertion end perimeter and a withdrawal end perimeter.

As used herein, the term "split cavity mold" is a mold comprised of two or more members that when brought together complete the inner cavity of the mold. Each member of the split cavity mold comprises at least a portion of the inner surface that when brought together or closed completes the mold structure. The split cavity mold is designed such that at least two or more of the mold members can be at least partially separated, if not fully separated, typically after the tampon has acquired a self-sustaining shape, to expand the cavity volume circumscribed by the inner surface(s) thus permitting the easier removal of the tampon from the mold. Partial separation can occur when only a portion of two mold members are separated while other portions of the two mold members remain in contact. Where each member's inner surface portion joins the inner surface portion of another member, those points of adjacency can define a straight line, a curve, or another seam of any convoluted intersection or seam of any regular or irregular form. The elements of the split cavity in some embodiments may be held in appropriate position relative to each other by linking elements of any form including bars, rods, linked cams, chains, cables, wires, wedges, screws, etc.

The term "stabilized," as used herein, refers to a tampon in a self-sustaining state wherein it has overcome the natural tendency to re-expand to the original size, shape and volume of the absorbent material and overwrap, which comprise the tampon pledget.

As used herein the term "tampon," refers to any type of absorbent structure that is inserted into the vaginal canal or other body cavities for the absorption of fluid therefrom, to aid in wound healing, or for the delivery of active materials, such as medicaments, or moisture. The tampon may be compressed into a generally cylindrical configuration in the radial direction, axially along the longitudinal axis or in both the radial and axial directions. While the tampon may be compressed into a substantially cylindrical configuration, other shapes are possible. These may include shapes having a cross section that may be described as rectangular, triangular, trapezoidal, semi-circular, hourglass, serpentine, or other suitable shapes. Tampons have an insertion end, withdrawal end, a length, a width, a longitudinal axis and a radial axis. The tampon's length can be measured from the insertion end to the withdrawal end along the longitudinal axis. A typical compressed tampon for human use is 30-60 mm in length. A tampon may be straight or non-linear in shape, such as curved along the longitudinal axis. A typical compressed tampon is 8-20 mm wide. The width of a tampon, unless otherwise stated in the specification, corresponds to the length across the largest cylindrical cross-section, along the length of the tampon.

The term "vaginal cavity," "within the vagina," and "vaginal interior," as used herein, are intended to be synonymous and refer to the internal genitalia of the mammalian female in the pudendal region of the body. The term "vaginal cavity" as used herein is intended to refer to the space located between the introitus of the vagina (sometimes referred to as the sphincter of the vagina or hymeneal ring,) and the cervix. The terms "vaginal cavity," "within the vagina" and "vaginal interior," do not include the interlabial space, the floor of vestibule or the externally visible genitalia.

As used herein, "cm" is centimeter, "g" is grams, "g/m$^2$" is grams per meter squared, "L" is liters, "L/s" is liters per second, "mL" is milliliters", "mm" is millimeters, "min" is minutes, "rpm" rate per minute, and "s" is seconds.

FIG. 1 and FIG. 2 show cross sections of a unitary embodiment of the permeable mold with a longitudinal axis L. The structure of the unitary mold 24 is a one piece mold so arranged as to define a space or inner cavity 26 for shaping a tampon pledget 20 (not shown) during compression and/or retaining the shape for a compressed tampon pledget 20 subsequent to compression during the stabilization process. The inner cavity 26 has an open proximal end 28 and a closed distal end 30. In the unitary embodiments of the permeable mold, the open proximal end 28 is used for both an ingress port wherewith the tampon pledget 20 is introduced into the inner cavity 26 and an egress port wherewith the tampon pledget 20 can be extracted from the inner cavity 26. In the embodiment shown in FIG. 1, the unitary mold 24 has pores 22 located axially along the unitary mold 24, the pores 22 are shown at the closed distal end 30. As shown in FIG. 2, the unitary mold 24 has pores 22 located radially along the unitary mold 24.

Figure 3:
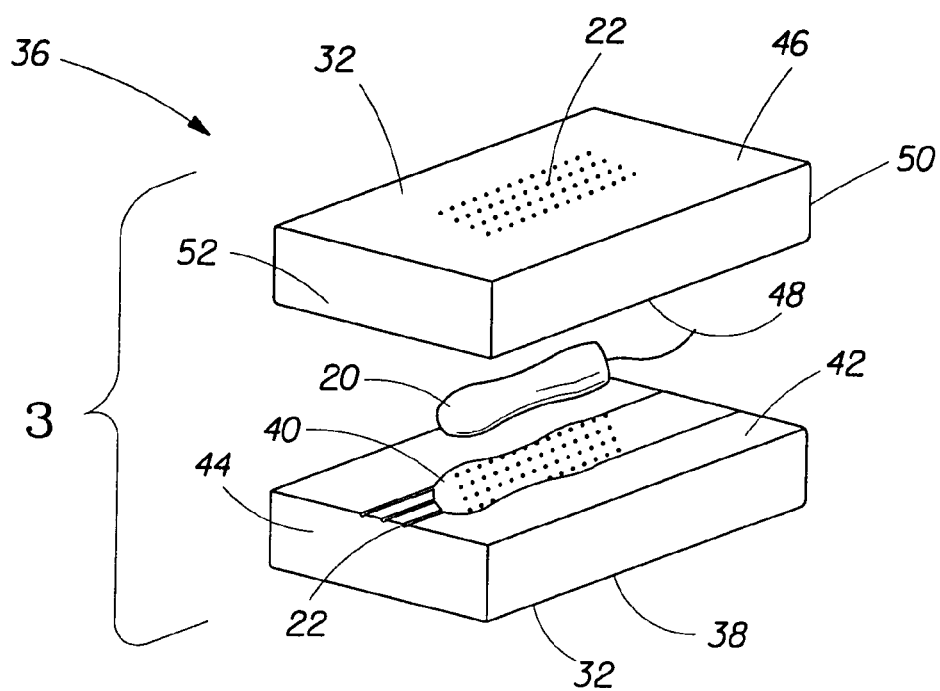
FIG. 3 is an exploded view of the split cavity mold with the compressed tampon pledget positioned between the first split cavity mold member and the second split cavity mold member.

FIG. 3 shows an exploded view of the split cavity mold 36 with the compressed tampon pledget 20 positioned between the first split cavity mold member 38 and the second split cavity mold member 46. The first split cavity mold member 38 and second split cavity mold member 46 are combined to form a split cavity mold 36. The first split cavity mold member 38 has a first inner surface 40 and an outer mold surface 32. The second split cavity mold member 46 is substantially similar, if not a mirror image or not identical in size, shape, and dimension to the first split cavity mold member 28 and has a second inner surface 48 and an outer mold surface 32. The first split cavity mold member 38 and the second split cavity mold member 46 are configured such that the first end 42 and the second end 44 of the first split cavity mold member 38 corresponds to the first end 50 and the second end 52 of the second split cavity mold member 46, such that, the first inner surface 40 and the second inner surface 48 face toward each other. These inner surfaces make up an inner cavity that is the desired shape of the compressed tampon pledget 20. In the embodiment shown, both the first split cavity mold member 38 and the second split cavity mold member 46 have pores 22 located axially and radially along the mold.

The mold can be constructed from permeable materials or can be fabricated from impermeable or permeable materials then modified either mechanically, chemically, or electrically to become permeable. Materials for the mold may include metals, polymers and/or composites. Embodiments of the mold that are comprised of metals may include steel, stainless steel, copper, brass, titanium, alloys, aluminum, anodized aluminum, titanium and combinations thereof. Embodiments of the mold that are comprised of polymers may include TEFLON® (E.I du Pont de Nemours and Company), polyethylene, polypropylene, polyester, polyolefins, polycarbonates, nylons, polyvinyl chloride, and mixtures thereof. One embodiment of a mold may be made of DELRIN® made by DuPont Plastics (Wilmington, Del. USA). Embodiments of the mold that are comprised of composites may include carbon fibers and blends of metal, epoxy, ceramic and polymer blends. Other examples of suitable materials for the mold are foamed metals or plastics. The mold may be made of aluminium and epoxy porous aggregate, such as METAPOR BF100Al, available from Portec Ltd, Switzerland. Pores 22, interstices, or pathways can be mechanically produced in the above materials by any mechanical operation known in the art including, but not limited to, operations such as drilling, milling, punching, casting, injection molding, and the like. Chemical modification techniques may include acid etching. Electrical modification techniques may include electrical discharge machining.

In several embodiments used with the process of the present invention, the tampon pledget is maintained within a mold that comprises at least one pore 22 along the length of the mold. The mold may have a plurality of pores 22 in some embodiments. The pores 22 can be on any location on the mold. In embodiments in which the mold is cylindrical, the pores 22 may be located radially, axially, or both radially and axially. These pores 22 may be macroscopic, microscopic or sub-microscopic. In some embodiments, the pores 22 may range in diameter from about 0.2 mm to about 1.5 mm.

The process of the present invention may be used for stabilizing any type of tampon known in the art including but not limited the tampon disclosed in U.S. Pat. No. 6,258,075 issued to Taylor, et al on Jul. 10, 2001 and the shaped tampons disclosed in U.S. patent application Ser. No. 10/150,050 entitled "Substantially Serpentine Shaped Tampon," and U.S. patent application Ser. No. 10/150,055, entitled "Shaped Tampon," both currently pending, commonly assigned, and filed on Mar. 18, 2002. Further, the process of the present invention may be used for the tampons having secondary absorbent members, disclosed in U.S. patent application Ser. No. 10/656,489, entitled "Absorbent Tampon Comprising A Secondary Absorbent Member Attached To The Outer Surface, filed on Sep. 5, 2003. U.S. Pat. No. 6,258,075 and U.S. patent application Ser. Nos. 10/150,050, 10/150,055, and 10/656,489 are hereby incorporated by reference herein.

The absorbent material that comprises the compressed tampon pledgets 20 may be constructed from a wide variety of liquid-absorbing materials commonly used in absorbent articles. Such materials include but are not limited to rayon (such as GALAXY Rayon SARILLE L rayon both available from Acordis Fibers Ltd., of Hollywall, England), cotton, folded tissues, woven materials, nonwoven webs, synthetic and/or natural fibers or sheeting, comminuted wood pulp which is generally referred to as airfelt, or combinations of these materials. Other materials that may be incorporated into the tampon pledget 20 including peat moss, absorbent foams (such as those disclosed in U.S. Pat. No. 3,994,298 issued to DesMarais on Nov. 30, 1976 and U.S. Pat. No. 5,795,921 issued to Dyer, et. al,) capillary channel fibers (such as those disclosed in U.S. Pat. No. 5,356,405 issued to Thompson, et. al on Oct. 18, 1994), high capacity fibers (such as those disclosed in U.S. Pat. No. 4,044,766 issued Kaczmarzk et al. on Aug. 30, 1977), superabsorbent polymers or absorbent gelling materials (such as those disclosed in U.S. Pat. No. 5,830,543 issued to Miyake, et al on Nov. 3, 1998). A more detailed description of liquid-absorbing materials shapes and dimensions can be found in U.S. patent application Ser. No. 10/039,979, filed Oct. 24, 2001, entitled "Improved Protection and Comfort Tampon," currently pending, and commonly assigned.

The compressed tampon pledget 20 stabilized by the process of the present invention may optionally include an overwrap comprising material such as, rayon, cotton, bicomponent fibers, polyethylene, polypropylene, other suitable natural or synthetic fibers known in the art, and mixtures thereof. In some embodiments, the tampon has a nonwoven overwrap comprised of bicomponent fibers that have a polypropylene core surrounded by polyethylene manufactured by Vliesstoffwerke Christian Heinrich Sandler GmbH & Co.KG (Schwarzenbach/Saale, Germany) under the tradename SAS B31812000. In other embodiments, the tampon may comprise a nonwoven overwrap of a hydroentangled blend of 50% rayon, 50% polyester available as BBA 140027 produced by BBA Corporation of South Carolina, U.S. The overwraps may be treated to be hydrophilic, hydrophobic, wicking or non-wicking.

The compressed tampon pledget 20 stabilized by the process of the present invention may optionally include a withdrawal cord, a secondary absorbent member, an additional overwrap, a skirt portion and/or an applicator. Withdrawal cords useful in the present invention may be made of any suitable material known in the prior art and include cotton and rayon. U.S. Pat. No. 6,258,075 to Taylor et al. entitled "Tampon with Enhanced Leakage Protection" describes a variety of secondary absorbent members for use in tampon pledgets 20. An example of a skirt portion is disclosed in U.S. patent application Ser. No. 09/993,988 entitled, "Tampon with Fluid Overwrap with Skirt Portion" currently pending, commonly assigned, and filed on Nov. 16, 2001.

Pressures and temperatures suitable for compression are well known in the art. Typically, the absorbent material and the overwrap are compressed in the radial direction and optionally axially by any means well known in the art. While a variety of techniques are known and acceptable for these purposes, a modified tampon compressor machine available from Hauni Machines, Richmond, Va., is suitable.

The compressed tampon pledget 20 stabilized by the present invention may be inserted digitally or insertion may be aided through the use of any prior art applicators. When the tampons are intended to be digitally inserted, it may be desirable to provide a finger indent made using a compression rod at the withdrawal end of the tampon to aid in insertion. An example of a finger indent is found in U.S. Pat. No. 6,283,952, entitled "Shaped Tampon" issued to Child, et al. on Sep. 4, 2000. Applicators that may be used are "tube and plunger" or "compact" type arrangements and may be plastic, paper, or other suitable material.

Figure 4:
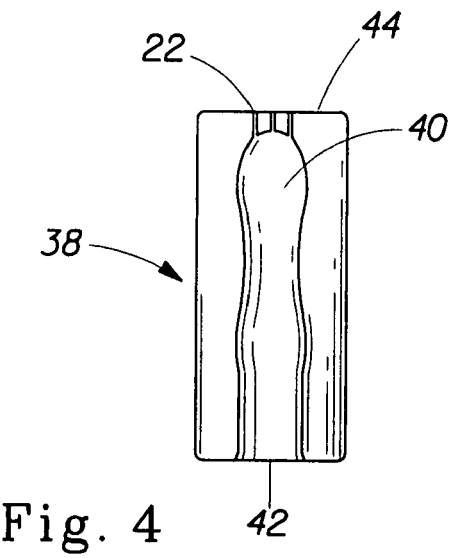
FIG. 4 is a plan view of a first split cavity mold member with pores located axially along the mold.
Figure 5:
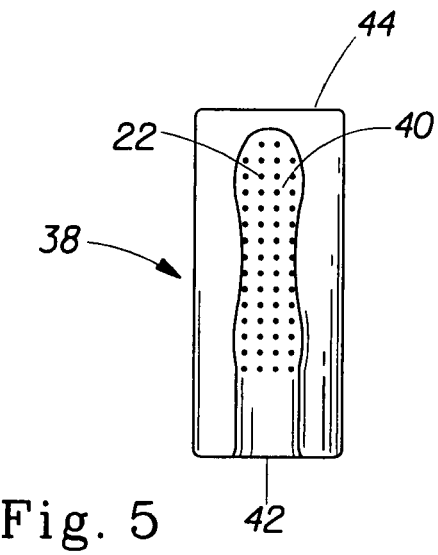
FIG. 5 is a plan view of a first split cavity mold member with pores located radially along the mold.

FIG. 4 and FIG. 5 show plan views of a first split cavity mold member 38 having a first inner surface 40 and an outer mold surface 32 (not shown). The first split cavity mold member 38 has a first end 42 and the second end 44. In the embodiment shown in FIG. 4, the first split cavity mold member 38 has pores 22 located axially along the first split cavity mold member 38. In the embodiment shown in FIG. 5, the first split cavity mold member 38 has pores 22 located radially along the first split cavity mold member 38.

Figure 6:
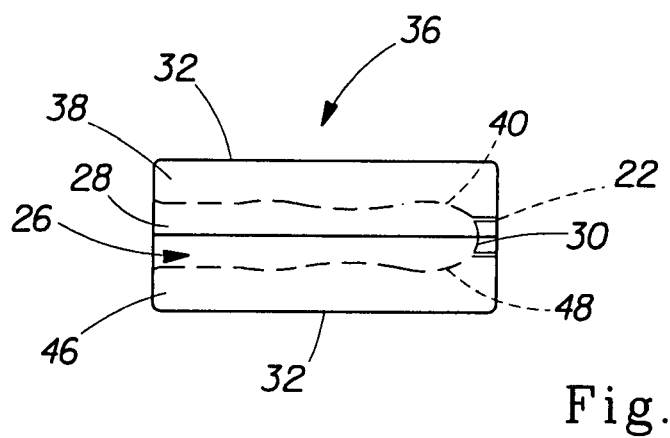
FIG. 6 is a side view of the split cavity mold with pores located axially along the mold.
Figure 7:
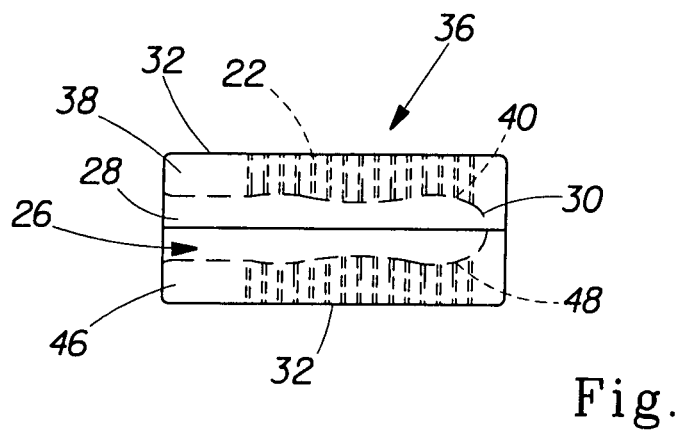
FIG. 7 is a side view of the split cavity mold with pores located radially along the mold.

FIG. 6 and FIG. 7 show a side view of the split cavity mold 36. The first split cavity mold member 38 and second split cavity mold member 46 are combined to form a split cavity mold 36. The first split cavity mold member 38 has a first inner surface 40 and an outer mold surface 32. The second split cavity mold member 46 is substantially similar, if not a mirror image or not identical in size, shape, and dimension to the first split cavity mold member 28 and has a second inner surface 48 and an outer mold surface 32. The first split cavity mold member 38 and the second split cavity mold member 46 are configured, such that, the first inner surface 40 and the second inner surface 48 face toward each other and define an inner cavity 26 for shaping a tampon pledget (not shown) during compression and/or retaining the shape for a compressed tampon pledget subsequent to compression during the stabilization process. The inner cavity 26 has an open proximal end 28 and a closed distal end 30. In some embodiments, such as embodiments that combine compression and stabilization, the open proximal end 28 may act as an ingress port wherein the tampon pledget 20 is introduced in the inner cavity. In the embodiment shown in FIG. 6, the split cavity mold 36 has pores 22 located axially along the split cavity mold 36. In the embodiment shown in FIG. 7, the split cavity mold 36 has pores 22 located radially along the split cavity mold 36.

Figure 8:
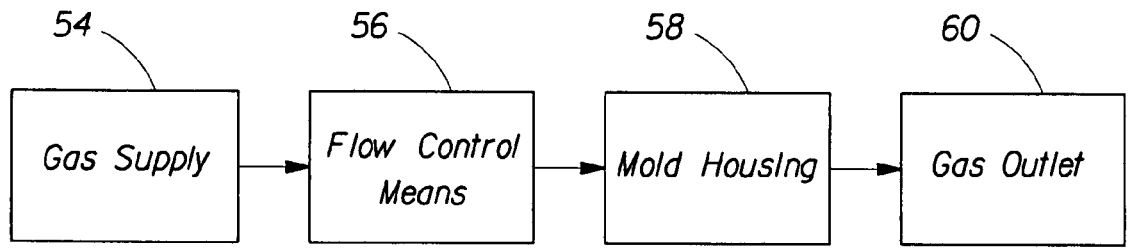
FIG. 8 is a diagram of one embodiment of a gas supply system in the process of the present invention.
Figure 9:
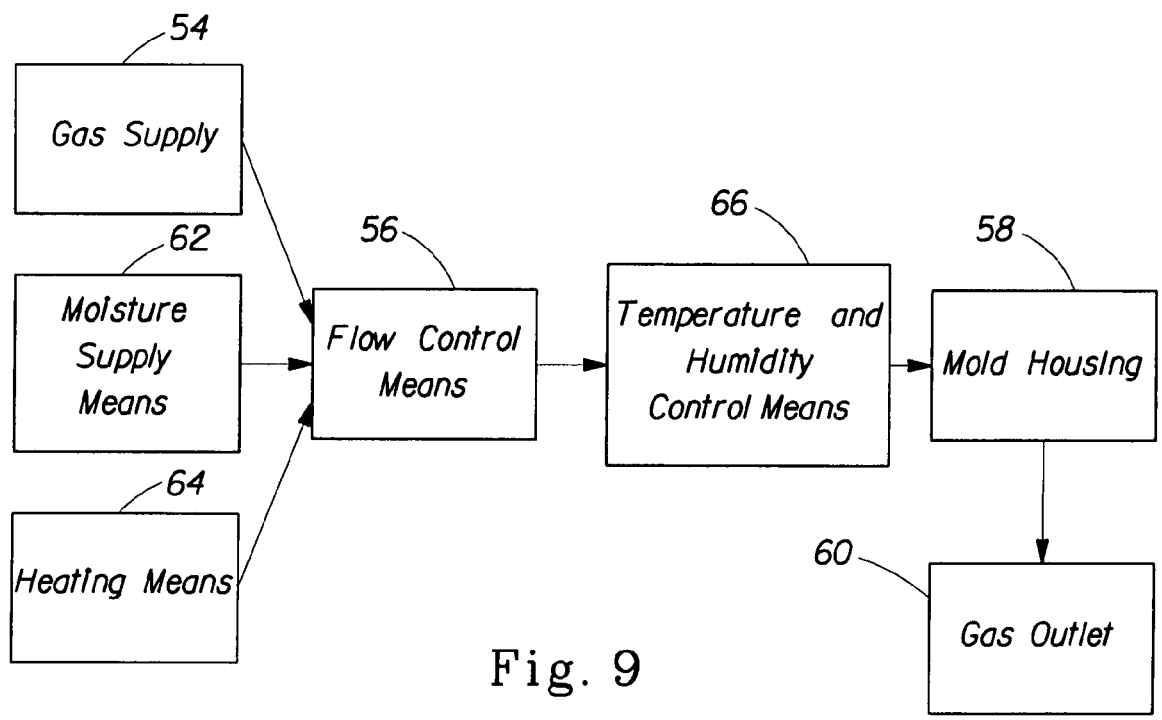
FIG. 9 is a diagram of another embodiment of a gas supply system of the process of the present invention.

FIG. 8 and FIG. 9 show a flow diagram of the process of the present invention. The process of the present invention comprises the steps of providing a compressed tampon pledget 20 and forcing gas through the compressed tampon pledget. The tampon pledget may be maintained within a permeable mold during this process. In some embodiments of the process, the stabilized compressed tampon may be produced in the presence of moisture. The moisture that is required in the process may be from the fibers of the material that comprises the tampon pledget 20 or within the gas that is introduced in the process or from both the moisture in the tampon pledget 20 and the gas that is introduced. In one embodiment of the process, the tampon pledget 20 that is provided may have an initial moisture content of the gas in the range of from 0 to about 30% water by weight as measured by the TAPPI method T 412, prior to the step of forcing gas through the tampon pledget. In another embodiment of the process, a tampon pledget is provided and the gas that is forced through the tampon pledget is humidified to a range from about 1% to about 100% relative humidity.

In another embodiment of the process, the stabilization process may be combined with a compression process. In these embodiments, the process for producing stabilized compressed tampons comprises the steps of providing a tampon pledget 20, providing a mold, compressing said tampon pledget 20 into the mold, forming a compressed tampon pledget, and forcing a gas into the mold to stabilize the compressed tampon pledget. In some embodiments, the mold provided is permeable. Another variation of this embodiment would be to partially compress the tampon pledget 20 and then have the final compression completed when pushing the tampon pledget 20 into the mold. For example, the process for stabilized tampons may be used in conjunction for the process disclosed in U.S. patent application Ser. No. 10/150,049, filed on Mar. 18, 2002, entitled "Method for Producing a Shaped Tampon" currently pending, commonly assigned, and filed on Mar. 18, 2002.

In all embodiments of the present process, the targeted moisture content of the tampon pledget 20 after the stabilization process is from about 4% to about 15% of water by weight, more typically from about 8 to about 10% water by weight as measured by the TAPPI method T 412.

The diagram in FIG. 8 shows that in some embodiments, the process can be accomplished by providing a gas supply 54 opposed to a gas outlet 60, and a mold housing 58 oriented there between that contains the tampon pledget 20 (not shown) within the permeable mold. The incoming gas enters the machine at the gas supply 54. The rate of the gas flow can be varied by a flow control means 56.

The gases forced into the tampon pledget 20 may be air, oxygen, nitrogen, argon, carbon dioxide, steam, ether, freon, inert gases and mixtures thereof. Typically, air is used. One inert gas that may be used to efficiently set the tampon is helium because helium has two times the heat transfer capacity of air. The supply of the gas may be varied by a flow control means 56. During the process of the present invention the gas may be propelled through the mold at a rate from about 0.2 to about 5.0 L/s. In some embodiments, the gas is propelled for time period ranging from about 1 s to about 20 s. In other embodiments, the gas is propelled for a time period ranging from about 1 s to about 10 s. In other embodiments, the gas is propelled from about 2 s to 8 s.

The process of the present invention may comprise the step of heating the gas that is introduced to the tampon pledget. The process of the present invention may comprise the step of humidifying the gas that is introduced to the tampon pledget. As shown in FIG. 9, a moisture supply means 62, heating means 64, and a temperature and humidity control means 66 is added to the diagram of FIG. 8. As such, the heated and humidified gas flows into the mold housing 58 oriented there between that contains the tampon pledget 20 (not shown) within the permeable mold and flows out the gas outlet 60.

In embodiments of the process where the gas is heated, a heating means 64 is used. The temperature may be varied by the temperature and humidity control means 66. In some embodiments, the gas is heated to a range of about 60° C. to about 210° C. In some embodiments, the gas may be heated to 100° C. and in other embodiments the gas may be heated to 163° C. In embodiments where the tampon pledget is maintained in a permeable mold, the molds may be heated prior to insertion of the tampon pledget 20 within the mold. The molds may be heated prior to insertion of the tampon pledget by hot air or alternate means, such as, by conductive heating prior to insertion of the tampon pledget 20. The mold can be heated from about 38° C. to about 210° C. In some embodiments, the molds may be heated to about 71° C. In some embodiments, the process may also comprise the step of cooling the tampon pledget. In some embodiments, the tampon pledget may be cooled by air to ambient room temperatures from about 21 to about 24° C. or less than 30° C.

In embodiments of the process where the gas is humidified, the moisture may be added via a moisture supply means 62. The humidity can be varied by a temperature and humidity control means 66. The moisture or humidity in the gas may be introduced by any know method in the art, including but not limited to atomization, evaporation, steam blending, super heated steam blending, supersaturated steam blending or the like. The gas may be humidified to a range from about 1% to about 100% relative humidity at the gas temperature.

In some embodiments of the process, the gas may be forced intermittently to stabilize the tampon pledget 20. This may include quick pulses of gas flow and includes the "treat" and "hold" method. In the treat and hold method, the tampon pledget 20 within the mold housing 58 is "treated" with gas being propelled through mold, this treatment is followed by a period where the tampon would be "held" within the mold without gas being propelled before the pledget 20 is extracted. In one embodiment of the process, the gas is propelled through the tampon within the mold, the tampon pledget 20 is "held" in the mold without gas being propelled, and gas is then propelled through the tampon again before the tampon pledget 20 is extracted. In another embodiment of the process, gas is propelled through the tampon within the mold, the tampon pledget 20 is "held" in the mold without gas being propelled, and then cool air is propelled through the tampon. In most embodiments of the treat and hold method, the compressed tampon pledget 20 is treated with propelled gas for a time period ranging from about 1 s to about 10 s, or from about 2 s to 8 s. The tampon is held for a time period ranging from about 1 s to about 15 s, or from about 2 s to about 10 s.

As apparent to one skilled in the art, the gas flow rates, temperature, pressure and composition can be varied while holding the tampon pledget in the mold housing 58 to achieve a desired result. For example, the humidity can be changed during the stabilization process. In some embodiments, the process may include a gas control and/or monitoring means to achieve targeted gas condition. Thus, entry and discharge gas conditions can be monitored. As well, entry and discharge gas conditions may be varied to control the flow, temperature, composition and pressure of the gas flow(s) to achieve a desired result.

The flow of gas can even be reversed either with the same or different gas composition such that the roles of the entry and discharge ports are reversed at least for a time. The process may include providing multiple gas supplies 54 and entry ports carrying gases with varied properties including by not limited to different compositions, temperature, flow rate, and pressure. These gas supplies 54 may be employed separately or concurrently. If desired during a portion or the entire process in some embodiments, suction or vacuum can be applied to either assist the flow of gas through the tampon or even lower the pressure in the mold. For example, the pressure inside the mold may be increased above atmospheric pressure for any given duration of time.

Beyond the need for stabilization, the flow of gas can be used to condition the tampon prior, subsequent, or during the stabilization process. Further the gas flow can be used to introduce adjustants into the product. These adjustants can be introduced prior, subsequent, or during the stabilization process. Adjustants may include medicaments, humectants, surface-active agents, lubricants, bactericides, fungicides, spermicides, perfumes, and other adjustants.

EXAMPLE 1

A tampon pledget is made comprising absorbent material and an overwrap. The absorbent material is made of 75% rayon and 25% cotton fiber with a basis weight of 780 g/m² having dimensions of about 70 mm in width and about 48 mm in length. The overwrap material is made of a nonwoven material comprising a hydroentangled blend of 50% rayon and 50% polyester having dimensions of about 168 mm in width and about 48 mm in length. The tampon pledget is made with a withdrawal means comprising cotton. The tampon pledget is then compressed axially and longitudinally to approximately 14 mm diameter and approximately 46 mm length. The tampon pledget is placed in a permeable mold. The permeable mold is unitary and has plurality of axial pores. The permeable mold containing the tampon pledget is placed in the mold housing of the machine. The air is heated to 100° C. and is humidified to 75% relative humidity. Air is propelled at 3.8 L/s (8 scfm) axially through the tampon pledget for 2 to 30 s. The tampon pledget is then extracted from the permeable mold.

EXAMPLE 2

A shaped tampon pledget is made according to the U.S. patent application Ser. No. 10/150,050, entitled "Substantially Serpentine Shaped Tampon." The tampon pledget is made comprising absorbent material and an overwrap. The absorbent material is 75% rayon and 25% cotton fiber with a basis weight of 780 g/m² having dimensions of about 70 mm in width and about 48 mm in length. The overwrap material is made of a bicomponent fiber having a polypropylene core surrounded by polyethylene having dimensions of about 168 mm in width and about 48 mm in length. The tampon pledget is then compressed axially and longitudinally to form a tampon pledget with a serpentine shape with continually changing cross-sectional areas and diameters along the length of 46 mm in a permeable mold having the same shape. The permeable mold is a split cavity mold that has plurality of radial and axial pores. The permeable mold is placed in the housing of the machine. The air is heated to 100° C. and was humidified to 75% relative humidity. Air is propelled 3.8 L/s (8 scfm) for 2-3 s. The tampon pledget is left in the mold or "held" for 5 s without the gas being propelled through the pledget before the pledget is extracted from the permeable mold.

EXAMPLE 3

A tampon pledget is made comprising absorbent material and an overwrap. The absorbent material is made of 100% GALAXY rayon having the dimensions of about 70 m in width and about 48 mm in length. The overwrap material is made of a nonwoven overwrap comprising a polypropylene core surrounded by polyethylene having dimensions of about 168 mm in width and about 48 mm in length. The tampon pledget is made with a withdrawal means comprising cotton. The tampon pledget is compressed axially and longitudinally to form a tampon pledget of approximately 14 mm diameter and approximately 46 mm length. The tampon pledget is placed in a permeable mold. The permeable mold is unitary and has plurality of axial pores. The permeable mold containing the tampon pledget is placed in the housing of the machine. The gas is heated to 100° C. and is humidified to 75%. Gas is propelled axially at 3.8 L/s (8 scfm) for 2-3 s. The then tampon is left in the mold or "held" for 5 s without the gas being propelled through the pledget. Cool air is then propelled at 5 s. The gas is cooled to 23° C. and is humidified to 50% relative humidity. The air was propelled for 1-2 s. The pledget is extracted from the mold.

EXAMPLE 4

A tampon pledget is made comprising absorbent material and an overwrap. The absorbent material is made of 75% rayon and 25% cotton fibers with a basis weight of 780 g/m² having dimension of about 70 mm in width and 48 mm in length. The overwrap is a nonwoven material comprising bicomponent fibers having a polypropylene core surrounded by polyethylene having dimensions of about 168 mm in width and about 48 mm in length. The tampon pledget also comprises a withdrawal means comprising cotton. The tampon pledget is compressed axially and longitudinally to form a tampon pledget of approximately 14 mm diameter and approximately 46 mm length. The tampon pledget is placed in a permeable mold. The permeable mold is a split cavity mold and has a plurality of radial pores. The permeable mold containing the tampon pledget is placed in the housing of the machine. The gas is heated to 100° C. and is humidified to 75% relative humidity. The gas is propelled radially at 3.8 L/s (8 scfm) for 2-3 s. The tampon pledget is then extracted from the permeable mold.

FIG. 10 is a simplified longitudinal cross-sectional view of one embodiment 100 of the process of the present invention, including a pair of split molds: a compression mold 102 and a stabilization mold 104. The embodiment 100 is particularly suitable for mass-production of stabilized tampons, wherein the steps of compressing and stabilizing of tampons are preferably separated in order to reduce the complexity of the apparatus producing stabilized tampons, especially, the tampons having a substantially serpentine shape and/or stabilized by the use of a gas.

Both the compression mold 102 and the stabilization mold 104 are shown in their open positions 128 and aligned with a pledget infeed carrier 106 and a tampon discharge carrier 108.

The embodiment 100 of FIG. 10 also shows a transfer member 110 and a pledget 112 disposed in the pledget infeed carrier 106. The transfer member 110 can serve several functions: (a) transferring the pledget 112 through the sequence of process steps taking place during traveling of the pledget 112 from the pledget infeed carrier 106 to the compression mold 102, to the stabilization mold 104, and to the tampon discharge carrier 108; (b) compressing the pledget 112 longitudinally (in addition to the compression in the radial direction provided by the compression die 102, as described below); (c) forming a desired shape cavity at the distal end of the tampon, suitable for the user's finger to facilitate digital insertion of the tampon into the vaginal cavity; and (d) providing a suitable seal for containing the gas inside the stabilizing die 104 during the stabilization treatment of the tampon, as described below.

The transfer member 110 preferably includes at least one needle 138 extending from the transfer member 110 longitudinally for discharging a stabilized tampon from the split stabilization mold 104, as will be described in more detail below.

As shown in FIG. 10, the transfer member 110 is aligned with the pledget infeed carrier 106, the compression mold 102, the stabilization mold 104, and the tampon discharge carrier 108 along a first longitudinal centerline L1.

It should be noted that the pledget having a secondary absorbent member extending from the distal end of the pledget (as noted above), should be loaded into the pledget infeed carrier with the secondary absorbent member being diverted radially in relation to the pledget to ensure that the secondary absorbent member does not interfere with the movement of the transfer member 110 in order to prevent pushing the secondary absorbent member into the distal end of the pledget. The radial diversion of the secondary absorbent member (preferably, together with at least one cord extending also from the distal end of the tampon) can be provided during loading of the pledget 112 by any suitable means, for example, a plate disposed in the direction of loading of the pledget into the cavity of the infeed carrier.

FIG. 11 is a simplified radial cross-sectional view of the pledget infeed carrier 106 of FIG. 10, taken along line 11-11. The pledget infeed carrier 106 includes a cavity 120 that can be suitably shaped to accept the pledget 112, which is shown as being folded to form an M-shape configuration. (It should be noted, however, that alternatively, the pledget 112 can be not folded or folded into any suitable configuration, including configurations comprising a multiplicity of folds ranging from 4 to 20 folds and greater. An exemplary embodiment of a gas-stabilized tampon having multiple folds for improved leakage protection and comfort through improved expansion characteristics is disclosed hereinafter.) The pledget infeed carrier 106 can be made from any material suitable for producing sanitary tampons.

FIG. 12 is a simplified radial cross-sectional view of the split compression mold 102 of FIG. 10, taken along line 12-12. The split compression mold 102 includes a first member 122 and a second member 124. At least one of the members 122 and 124 is capable of moving in a radial direction R to effect an open position 128 or a closed position 129 (shown as an interrupted line) of the split compression mold 102. In the closed position 129, the inner surface 127 of the compression mold 102 forms preferably a circular cross-section of a desired diameter, for example, a diameter D of 12.5 mm. However, the inner surface 127 can be of any suitable shape and of any desired dimension. The split compression mold 102 can be made from any materials capable of providing desired compression forces and suitable for producing sanitary tampons.

FIG. 13 is a simplified radial cross-sectional view of the split stabilization mold 104 of FIG. 10, taken along line 13-13. The split stabilization mold 104 can be similar in the dimensions and makeup, in all or any aspects, to the split mold 36 shown in FIGS. 3-7 and described in more detail above. For example, similarly to the split mold 36 of FIGS. 3-7, the split stabilization mold 104 includes the first member 38, the second member 46, and at least one pore 22 suitable for providing a gas flow inside the inner surface of the stabilization mold 104. The split stabilization mold 104 is shown in the open position 128 when the first member 38 and the second member 46 are separated from each other. At least one of the mold members 38 and 46 can move in the radial direction R to effect the open position 128 or the closed position 129 (shown as an interrupted line) when the first member 38 and the second member 46 are in contact with each other.

FIG. 14 is a simplified radial cross-sectional view of a tampon discharge carrier 108 of FIG. 10, taken along line 14-14. The tampon discharge carrier 108 includes a cavity 130 that can be suitably dimensioned and shaped to accept the compressed and stabilized tampon 20 (not shown here, but shown in FIG. 3)

In one embodiment of the present invention, the cavity 130 is defined by preferably a multiplicity of longitudinal flutes 133 to facilitate the dissipation of a gas forced into the cavity 130 during the stabilization process of the present invention. In addition, in one embodiment of the present invention (see FIG. 28), the tampon discharge carrier 108 can include preferably two opposing, spring-loaded plugs 135 penetrating into the cavity 130 for facilitating the retention of the tampon inside the cavity 130. The tampon discharge carrier 108 can be made from any material suitable for producing sanitary tampons.

Figure 15:
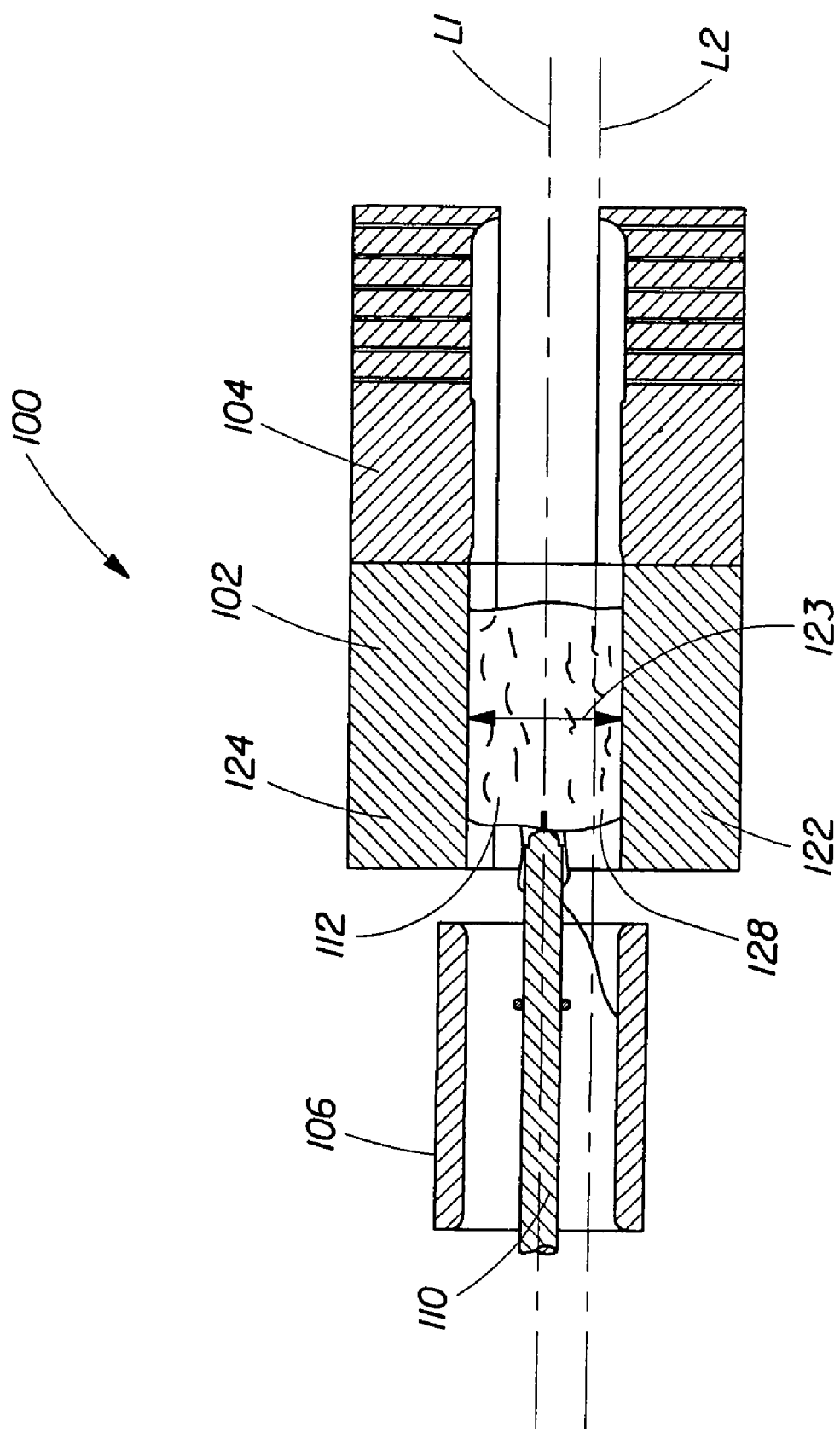
FIG. 15 is a simplified longitudinal cross-sectional view of the embodiment 100 of FIG. 10, showing the pledget being loaded into the split compression mold by a transfer member, the split compression mold being in an open position.

FIG. 15 is a simplified longitudinal cross-sectional view of the embodiment 100 of FIG. 10, showing the pledget 112 being loaded into the split compression mold 102 by the transfer member 110 when the split compression mold 102 is in the open position 128 and the transfer member 110 is aligned with the first longitudinal centerline L1. In the open position 129, the compression mold 102 has an inside dimension 123 that can be any dimension suitable for accepting the pledget 112. For example, in one embodiment of the invention, the inside dimension 123 is about 40.5 mm.

Figure 16:
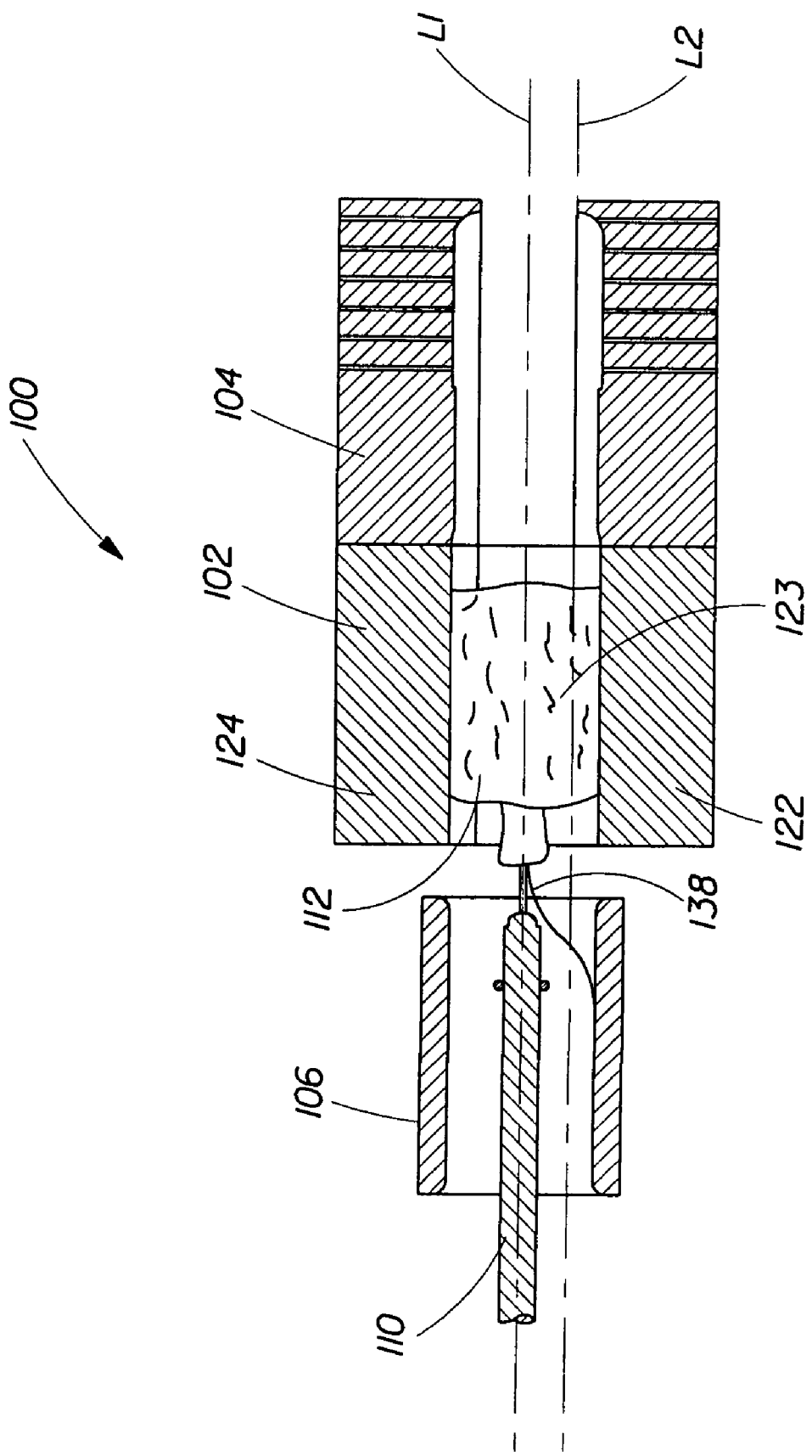
FIG. 16 is a simplified longitudinal cross-sectional view of the embodiment 100 of FIG. 15, showing a transfer member being detracted from the pledget.

FIG. 16 is a simplified longitudinal cross-sectional view of the embodiment 100 of FIG. 10, showing the transfer member 110 being retracted from the pledget 112 after the pledget 112 is loaded in the compression mold 102. It should be noted that the detraction of the transfer member from the pledget 112 is preferred in order to detract the needle(s) 138 from the pledget 112 prior to the next step of compression of the pledget 112. However, other contemplated embodiments of the transfer member 110 of the present invention can enable the needle(s) 138 to move inside the transfer member 110 to protrude from or hide inside the transfer member 110, thus, eliminating the need for the retraction of the transfer member 110.

It should be also noted that other contemplated embodiments of the split compression and stabilization molds 102 and 104, respectively, of the present invention can include both moving mold members, in contrast to the preferred embodiments including a moving mold member and a fixed mold member. When both moving mold members are employed, the transfer member 110 does not need to move in the radial direction R for closing and opening of the molds.

Figure 17:
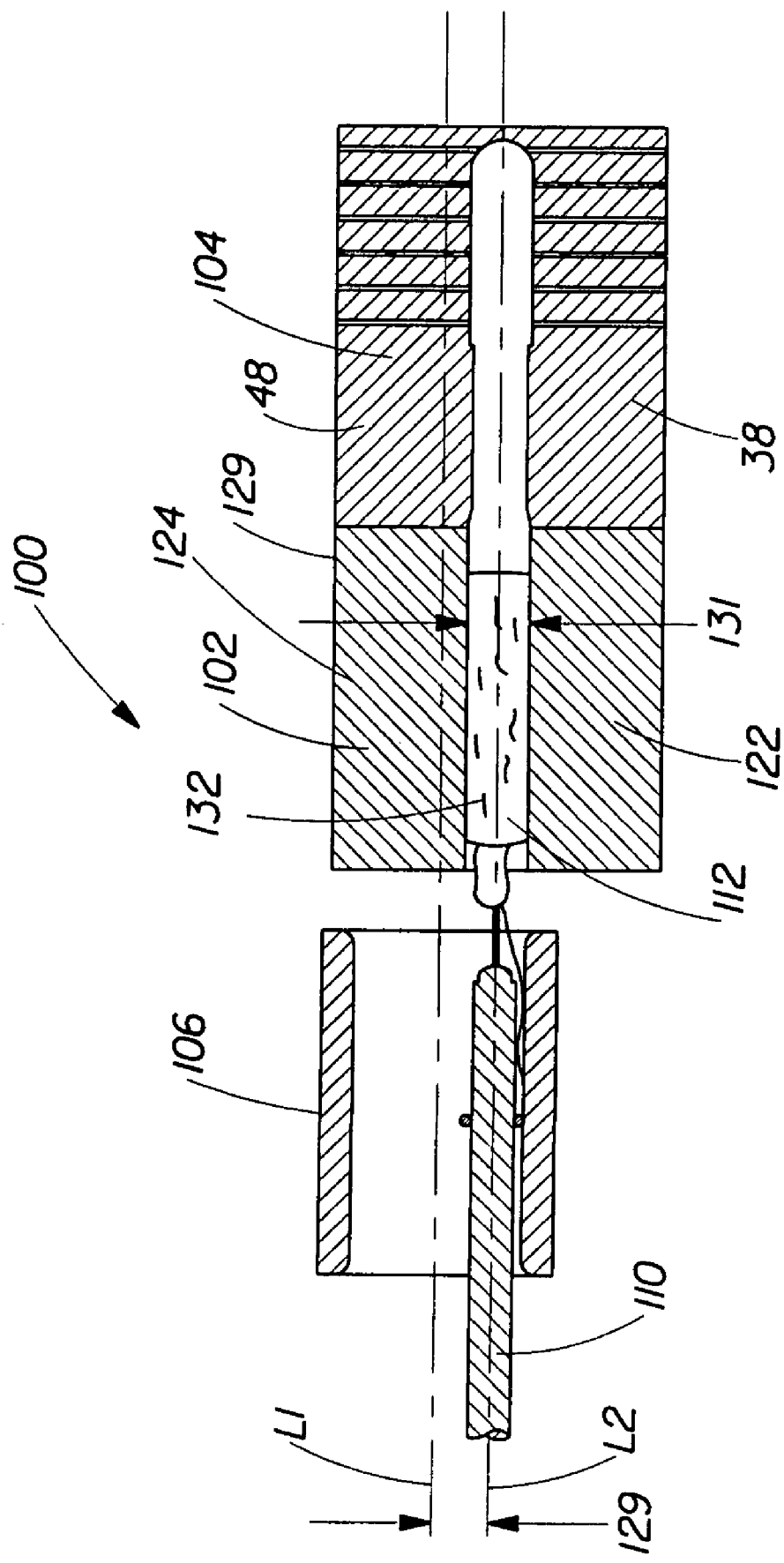
FIG. 17 is a simplified longitudinal cross-sectional view of the embodiment 100 of FIG. 16, showing the pledget being compressed into a compressed tampon in the compression mold.

FIG. 17 is a simplified longitudinal cross-sectional view of the embodiment 100 of FIG. 10, showing the pledget 112 being compressed into a compressed tampon 132 in the compression mold 102 when the compression mold 102 is in the closed position 129. In the closed position 129, the compression mold 102 has an inside dimension 131 that can be any dimension suitable for compressing the pledget 112 into a desired compressed dimension. For example, in one embodiment of the invention, the inside dimension 131 is about 12.5 mm.

The closed position 129 is preferably accomplished by moving the first compression mold member 122 in the radial direction R toward the second compression mold member 124. However, as noted above, other contemplated embodiments of the present invention can include both moving mold members. During the closing of the compression mold 102, the pledget 112 undergoes a radial compression in the direction R, reducing the radial dimension of the pledget to the inside dimension 131, for example, 12.5 mm. Thus, in the particular example, the first compression mold member 122 moved radially about 40.5 mm–12.5 mm=28 mm.

As shown in FIG. 17, the transfer member 110 also moved in the radial direction R to 30, become aligned along a second longitudinal centerline L2 aligned with the closed position 129 of the compression mold 102. The distance between the first longitudinal centerline L1 and the second longitudinal centerline L2 is a dimension 129, which is preferably about half of the radial movement of the first compression mold member 122. For example, in the particular example above, when the first compression mold member 122 moves about 28 mm, the transfer member 112 moves the distance 129 of about 14 mm.

Figure 18:
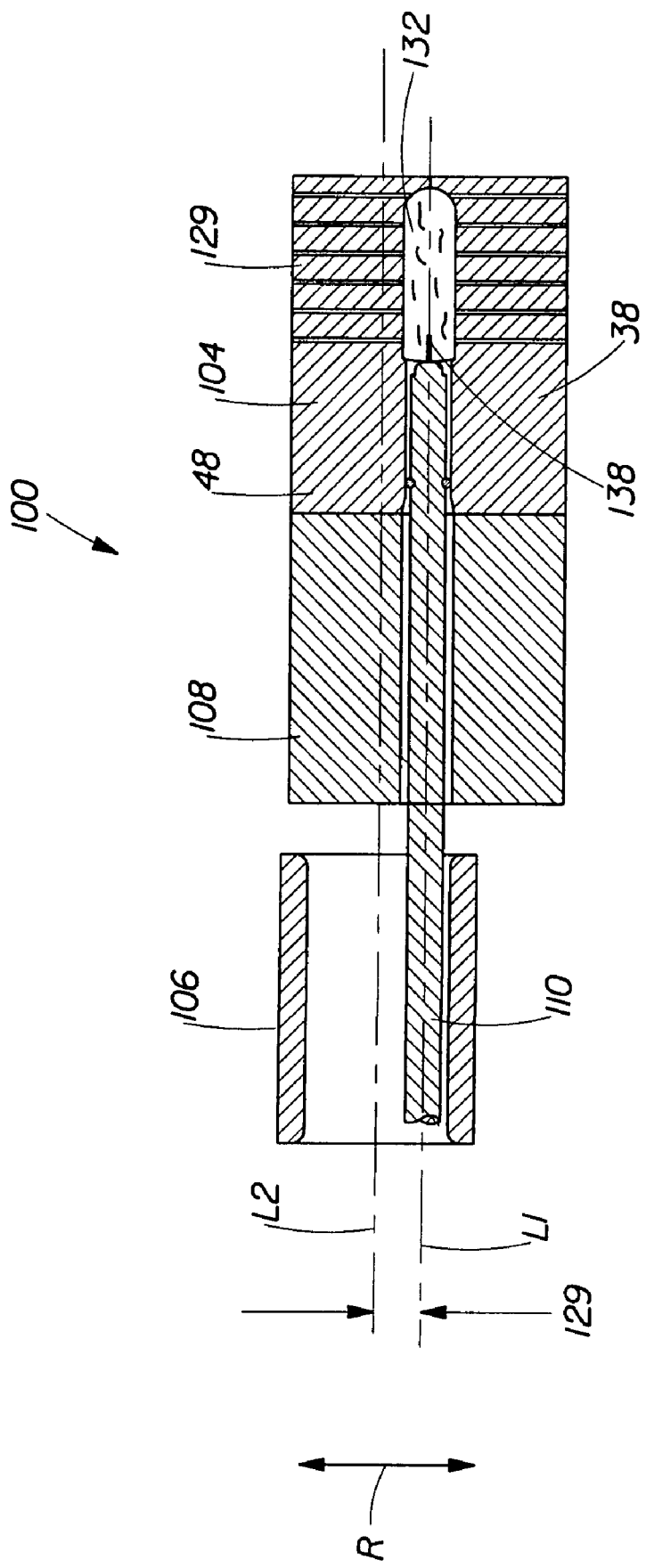
FIG. 18 is a simplified longitudinal cross-sectional view of the embodiment 100 of FIG. 17, showing the compressed tampon being loaded into the stabilization mold, the stabilization mold being closed.

FIG. 18 is a simplified longitudinal cross-sectional view of the embodiment 100 of FIG. 10, showing the compressed tampon 132 being loaded into the split stabilization mold 104 by the transfer member 110, when the split stabilization mold 104 is preferably in the closed position 129 and aligned with the second longitudinal centerline L2. In a preferred embodiment, the closed position 129 of the stabilization mold 104 is accomplished by moving the first member 38 of the stabilization mold 104 in the radial direction R simultaneously with the first compression mold member 122, as shown in FIG. 17. However, as was noted above with respect to the compression mold 102, the stabilization mold 104 can also include two moving mold members. Furthermore, in other contemplated embodiments of the present invention, the compression mold 102 and the stabilization mold 104 do not need to close and open simultaneously.

As noted above, the transfer member 110 preferably includes at least one needle 138 extending from the transfer member 110 longitudinally. The needle(s) 138 are capable of penetrating into the compressed tampon 132 to enable a subsequent discharge of the stabilized tampon 136 from the stabilization mold 104. The number of needles 138 can include any suitable number, preferably two needles to prevent turning of the tampon around a single needle around a longitudinal direction of the tampon.

Figure 20:
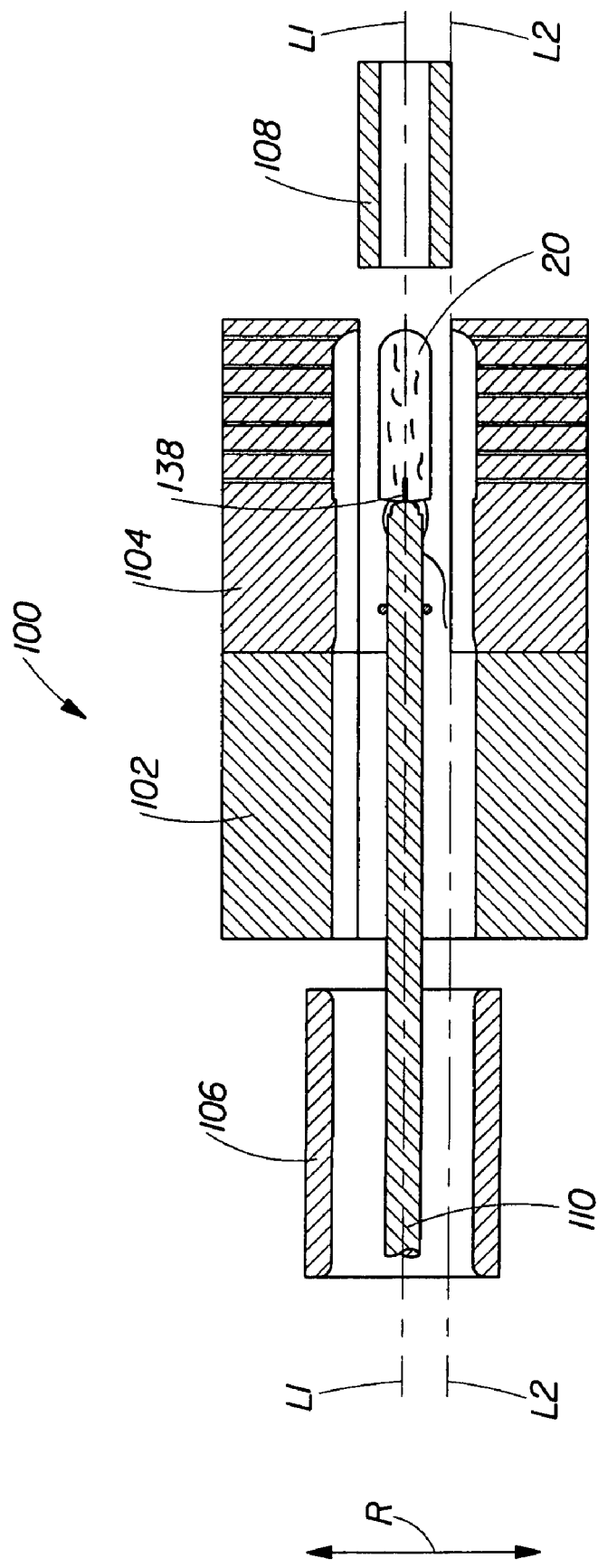
FIG. 20 is the a simplified longitudinal cross-sectional view of the embodiment 100 of FIG. 19, showing the stabilized tampon held by the transfer member inside the open stabilized mold.

The needle(s) 138 can have a relatively sharp point to provide penetration of the needle(s) 138 into the compressed tampon 132 without damaging the tampon 132. The needle(s) 138 can be of any suitable diameter, for example, between 1-2 mm, extending from the transfer member 110 at any suitable length sufficient to hold the tampon, as shown in FIG. 20, for example, 12 mm.

Figure 18A:
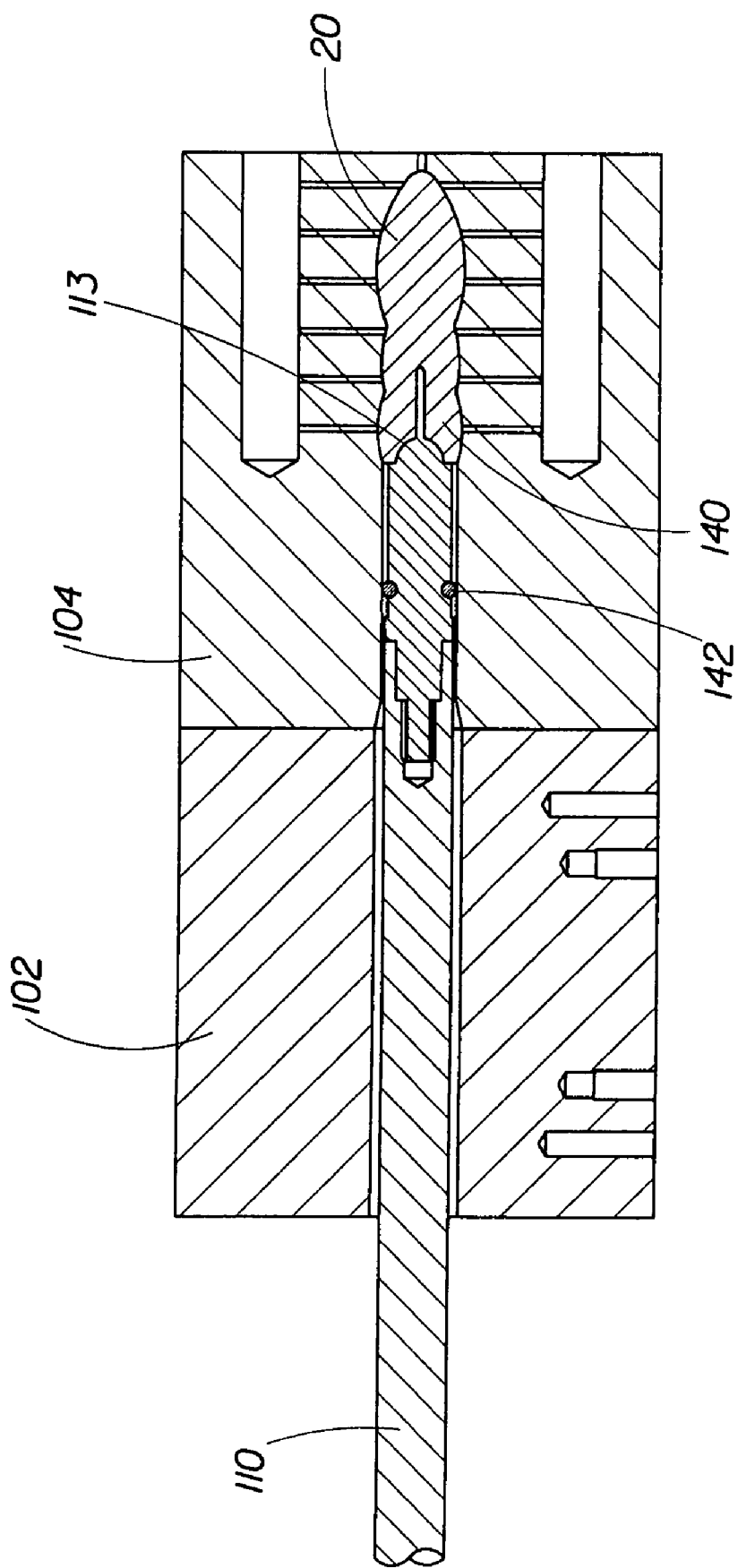
FIG. 18A is a more detail cross-sectional view of the stabilization mold and the transfer member penetrating the stabilized tampon inside the stabilization mold.

FIG. 18A is a more detail cross-sectional view of one embodiment of the transfer member 110 penetrating the stabilized tampon 20 inside the stabilization mold 104. The transfer member 110 can include a tip 113 suitably shaped to form a cavity 140 in the distal end of the tampon 20, suitable for the user's finger to facilitate digital insertion of the tampon into the vaginal cavity. The tip 140 can also include a seal 142 capable of sealing the cavity of the stabilization mold 104 to contain the gas that will be injected into the inside of the stabilization mold 104 during the next step of the stabilization treatment of the tampon, as described below and shown in FIG. 19.

Figure 19:
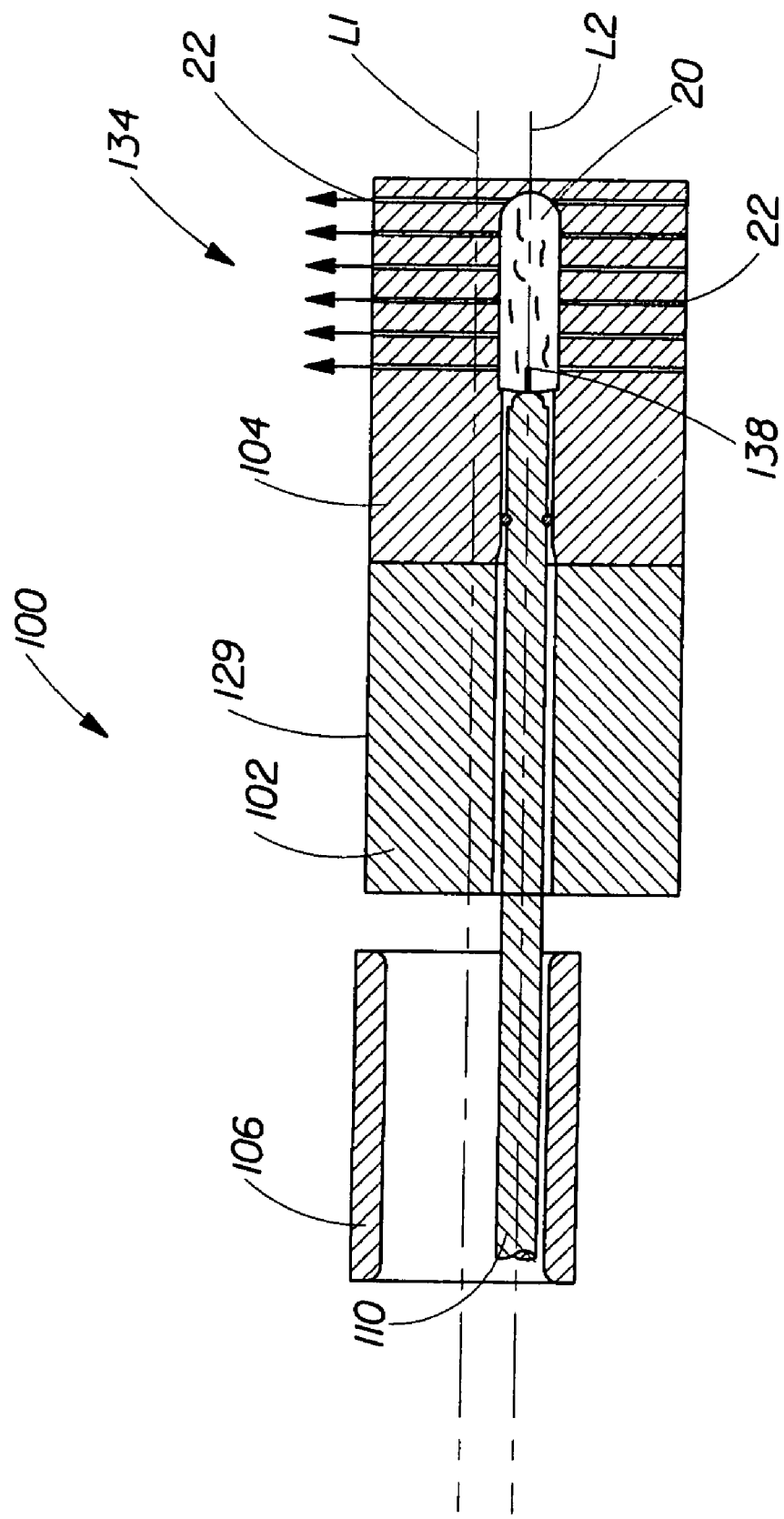
FIG. 19 is a simplified longitudinal cross-sectional view of the embodiment 100 of FIG. 18, showing the compressed tampon being subjected to a gas flow in the stabilization mold to form a stabilized tampon.

FIG. 19 is a simplified longitudinal cross-sectional view of the embodiment 100 of FIG. 10, showing the compressed tampon 132 being subjected to a gas flow 134 provided through at least one pore 22 of the stabilization mold 104 to form a stabilized tampon 20. The transfer member 110 is aligned with the second longitudinal centerline L2 aligned with the closed position 129 of the stabilization mold 104. The process conditions suitable for stabilizing the tampons, including tampon materials, gases, temperature, humidity, time, and the like are disclosed in detail above. Specifically, with respect to the temperature of the stabilizing mold 104, it is preferable to maintain the stabilizing mold 104 at elevated temperature of about 50 deg. C. to about 150 deg. C., preferably of about 100 deg. C. to about 130 deg. C., to prevent condensation of a gas, for example, a steam inside the stabilization mold 104. The desired temperature of the stabilization mold 104 can be provided by any suitable means including, for example, electric cartridge heaters.

During the supplying of the gas flow 134, the gas flow 134 is supplied through a pressurized side of the stabilization mold 104 and vented through a venting side of the stabilization mold into the atmosphere to provide a flow of the gas through the tampon inside the stabilization mold. The gas flow and venting can range from about 0.5 s to about 5 s, preferably from about 0.5 s to about 1.5 s.

FIG. 20 is a simplified longitudinal cross-sectional view of the embodiment 100 of FIG. 10, showing the stabilized tampon 20 being stripped from the inner surface of the stabilization mold 104 and held by the needle(s) 138 of the transfer member 110 inside the stabilization mold 104 when the stabilization mold 104 is returned to the open position 128 (i.e., aligned with the first longitudinal centerline L1) and the transfer member 110 is returned to be aligned with the first longitudinal centerline L1.

As noted above, the transfer member 110 preferably includes at least one needle 138 extending from the transfer member 110 longitudinally. The needle(s) 138 are capable of penetrating into the compressed tampon 132 to enable a subsequent discharge of the stabilized tampon 136 from the stabilization mold 104. The number of needles 138 can include any suitable number, preferably two needles to prevent turning of the tampon around a single needle around a longitudinal direction of the tampon.

The needle(s) 138 can have a relatively sharp point to provide penetration of the needle(s) 138 into the compressed tampon 132 without damaging the tampon 132. The needle(s) 138 can be of any suitable diameter, for example, between 1-2 mm, extending from the transfer member 110 at any suitable length sufficient to hold the tampon, for example, 12 mm.

It should be noted that the above method of unloading stabilized tampons by the use of a transfer member having at least one, preferably two needles, can be applicable for unloading tampons not only from a stabilization mold utilizing a gas flow, but also for any type of a stabilization mold, for example, utilizing conductive heating, microwave heating, and the like.

Figure 21:
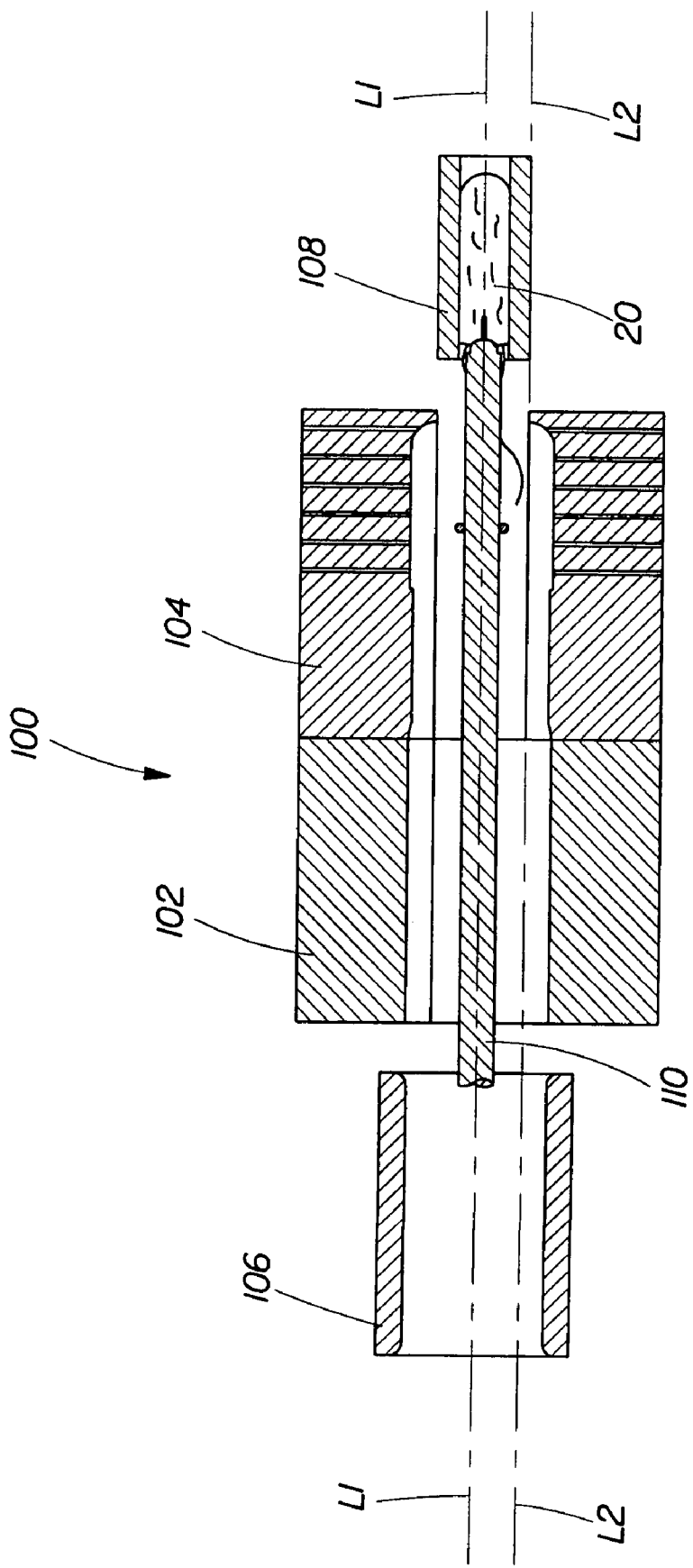
FIG. 21 is a simplified longitudinal cross-sectional view of the embodiment 100 of FIG. 20, showing the stabilized tampon being loaded into a tampon discharge carrier by the transfer member.

FIG. 21 is a simplified longitudinal cross-sectional view of the embodiment 100 of FIG. 10, showing the stabilized tampon 20 being loaded into the tampon discharge carrier 108 by the transfer member 110. The transfer member 110 remains aligned with the first longitudinal centerline L1.

Figure 22:
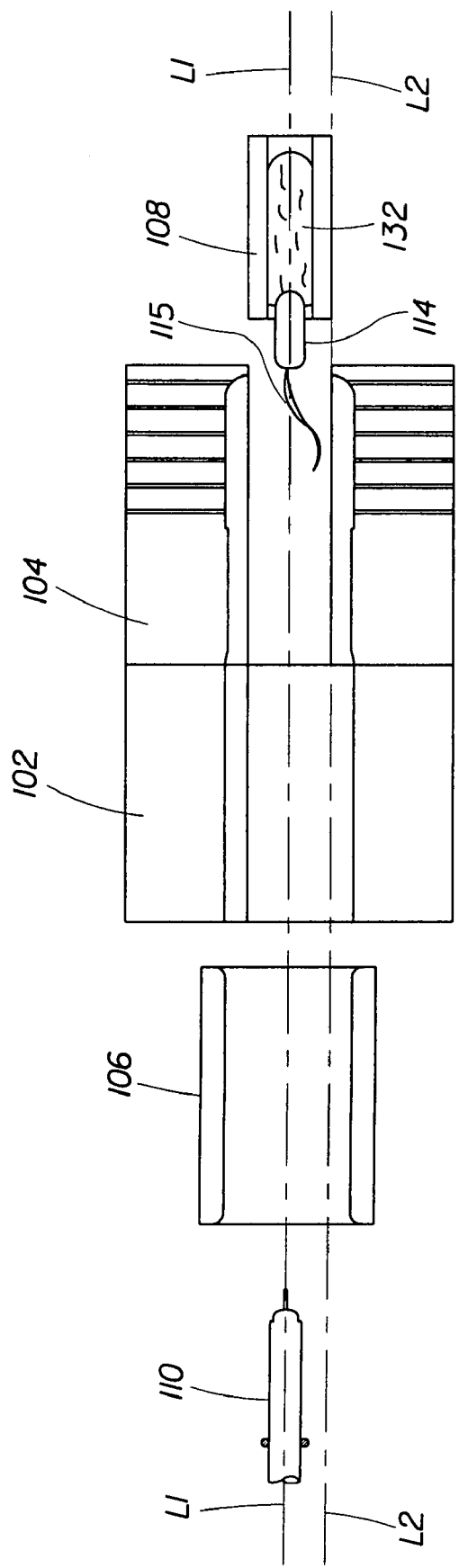
FIG. 22 is a simplified longitudinal cross-sectional view of the embodiment 100 of FIG. 21, showing the transfer member retracted from the stabilized tampon.

FIG. 22 is a simplified longitudinal cross-sectional view of the embodiment 100 of FIG. 10, showing the transfer member 110 being retracted from the stabilized tampon 20 and aligned with the first longitudinal centerline L1. The stabilized tampon 20 remains in the tampon discharge carrier 108 for further transferring to downstream processing, such as, for example, wrapping and packaging.

Figure 23:
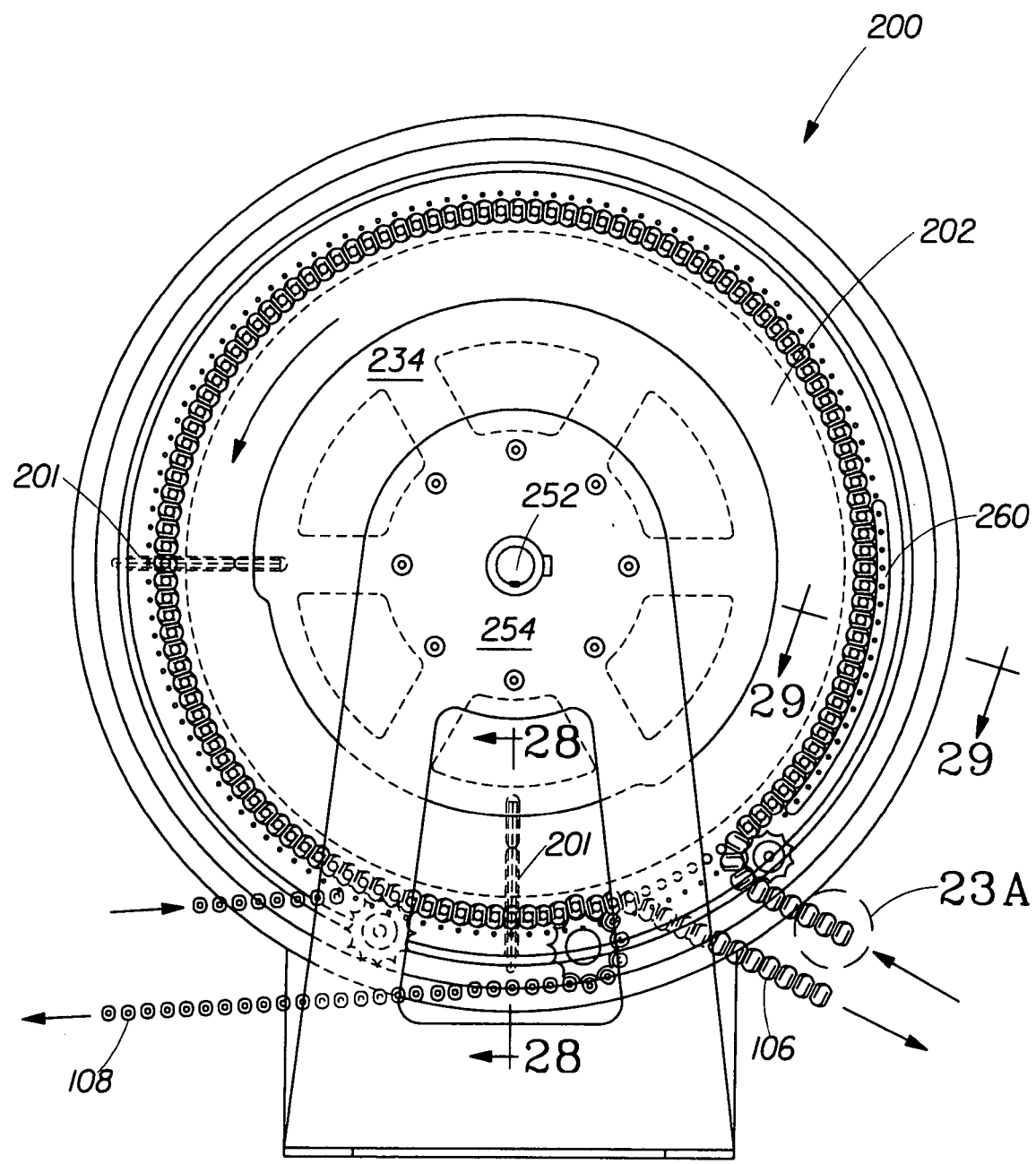
FIG. 23 is a simplified front elevation view of a rotary apparatus of the present invention suitable for mass-production of stabilized tampons by utilizing the steps of the method of the present invention shown in FIGS. 15-22, showing, for clarity, only one of the multiple tooling stations.

FIG. 23 is a simplified front elevation view of one embodiment of a rotary apparatus 200 of the present invention suitable for the mass-production of stabilized tampons by utilizing the steps of the method of the present invention shown in FIGS. 15-22 and described above. It should be noted that other embodiments of the rotary apparatus utilizing the steps of the method of the present invention shown in FIGS. 15-22 and described above have been contemplated by the Applicants.

The rotary apparatus 200 includes a multiplicity of tooling stations 201 disposed around the perimeter of the rotary apparatus 200 (for the clarity of the figure, only two tooling stations 201 are shown in FIG. 23). However, the number of tooling stations 201 can be any suitable number, wherein each tooling station 201 is capable of producing a single stabilized tampon during a single revolution of the rotary apparatus 200.

The rotary apparatus 200 further includes the pledget infeed carrier 106 for providing pledgets 112 (as shown in FIG. 11). The pledget infeed carrier 106 and the pledgets 112 were described above and exemplary cross-sectional embodiments of both are shown in FIG. 1. The rotary apparatus 200 further includes the tampon discharge carrier 108 for discharging stabilized tampons 20 (as shown in FIG. 22).

Figure 23A:
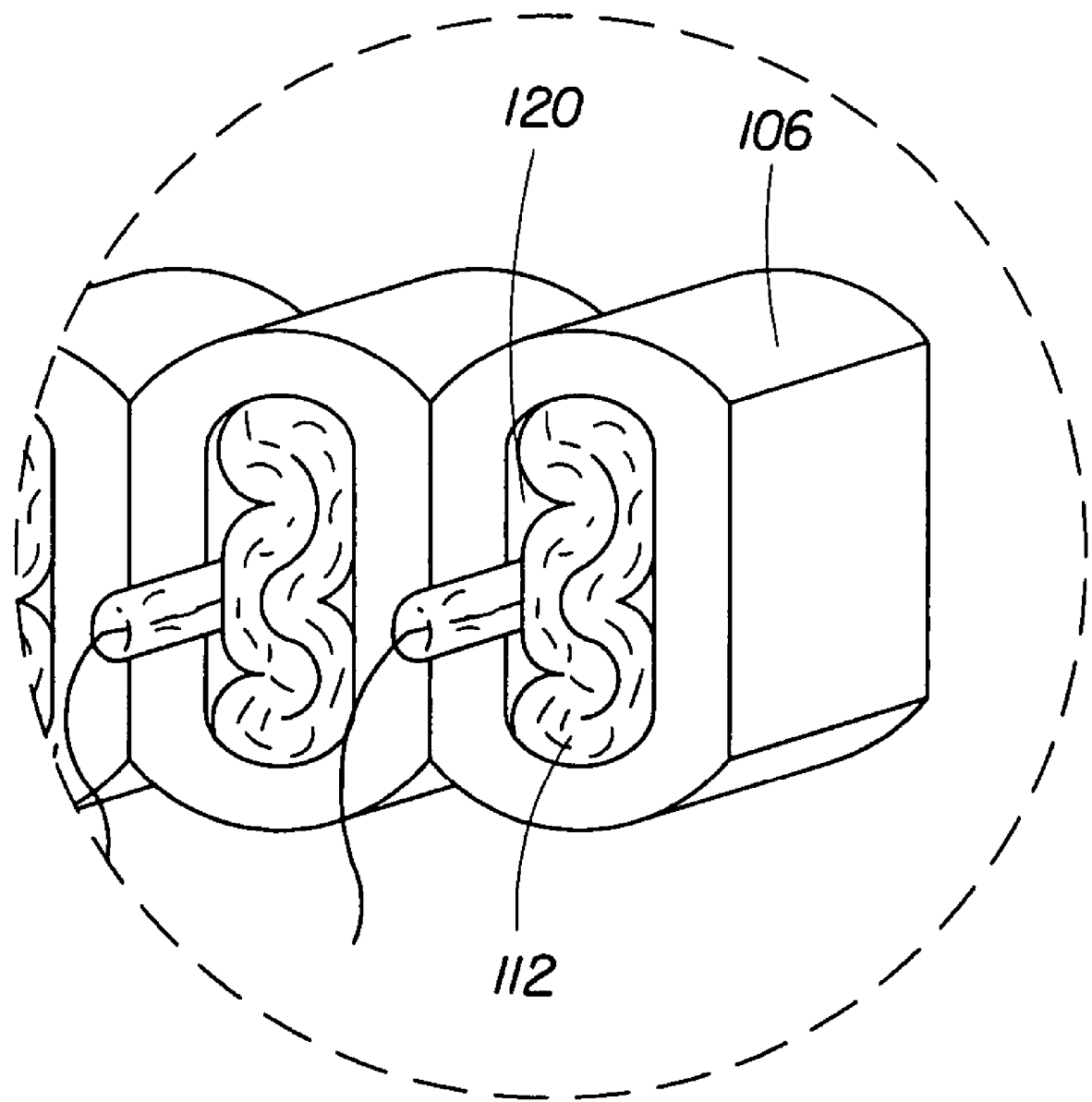
FIG. 23A is a magnified perspective view of an infeed carrier cavity of FIG. 23, containing an M-folded pledget.

FIG. 23A is a magnified perspective view of an infeed carrier cavity 120 of FIG. 23, containing an M-folded pledget. The pledget infeed carrier 106 includes a cavity 120 that can be suitably shaped to accept the pledget 112, which is shown as being folded to form an M-shape configuration. However, alternatively, the pledget 112 can be not folded or folded into any suitable configuration. The pledget infeed carrier 106 can be made from any material suitable for producing sanitary tampons.

Figure 24:
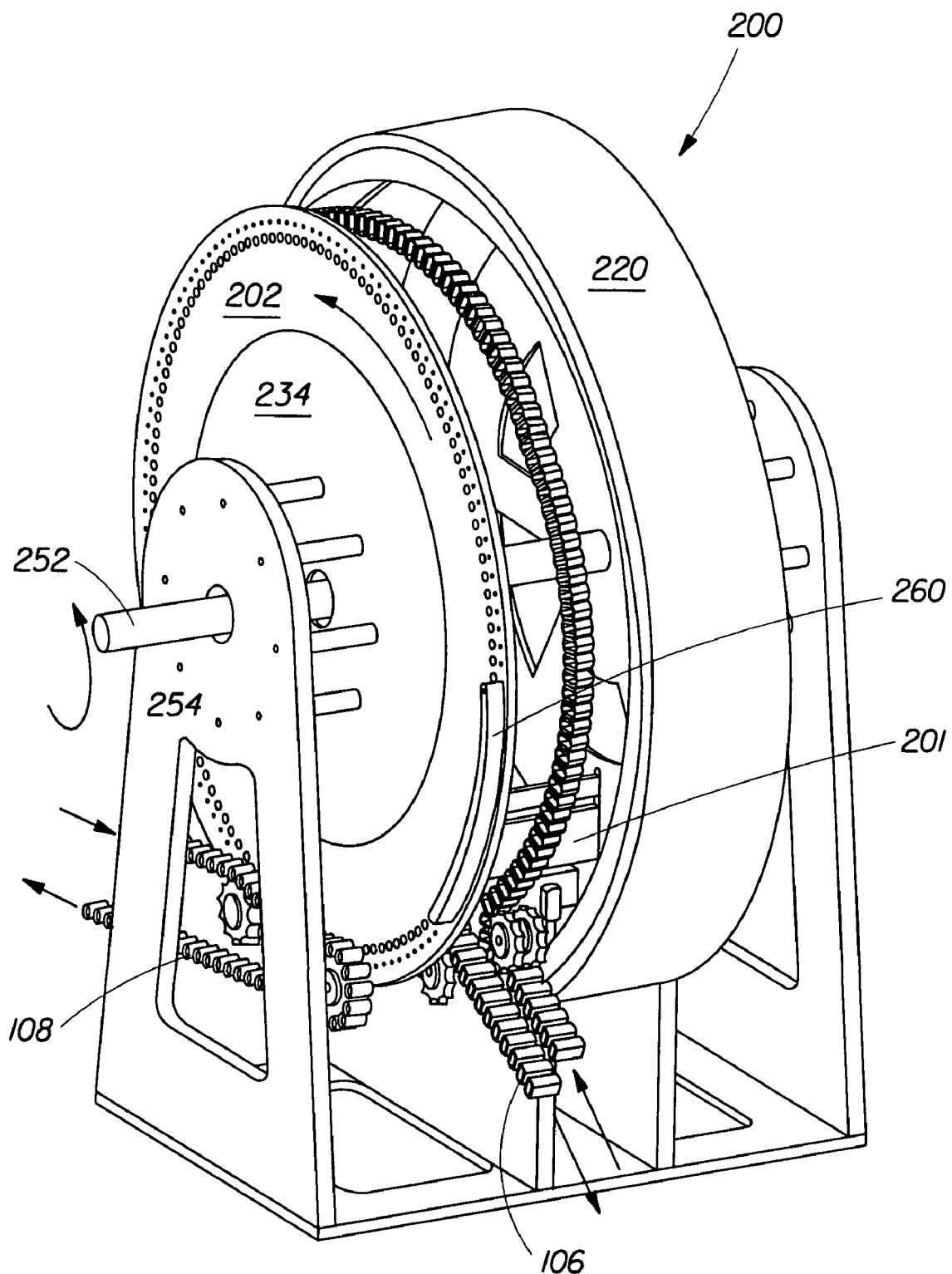
FIG. 24 is a simplified perspective view of the rotary apparatus of FIG. 23.

FIG. 24 is a simplified perspective view of the rotary apparatus 200 of FIG. 23 showing a stationary frame 254 and fixedly attached stationary cams, for example, two opposing mold-closing cams 234 and 236 (only one mold closing cam 234 is shown in this view; see FIG. 25 for the other mold-closing cam 236) and a cylindrical cam 220 having an inside track 222 (not shown in this view; see FIGS. 25, 26, and 29) for activating the transfer member 110. It should be noted, however, that the number of cams 234, 236, and 220 can vary; furthermore, instead of utilizing the cams 234, 236, and 220, the molds 102 and 104 and the transfer member 110 can be alternatively activated by any suitable means, including servomotors and the like.

The frame 254 is rotationally connected with a shaft 252 capable of rotating drum side plates 202 and 211 (not shown in this view; see FIGS. 25 and 28) carrying a multiplicity of tooling stations 201 inside the rotary apparatus 200.

Figure 25:
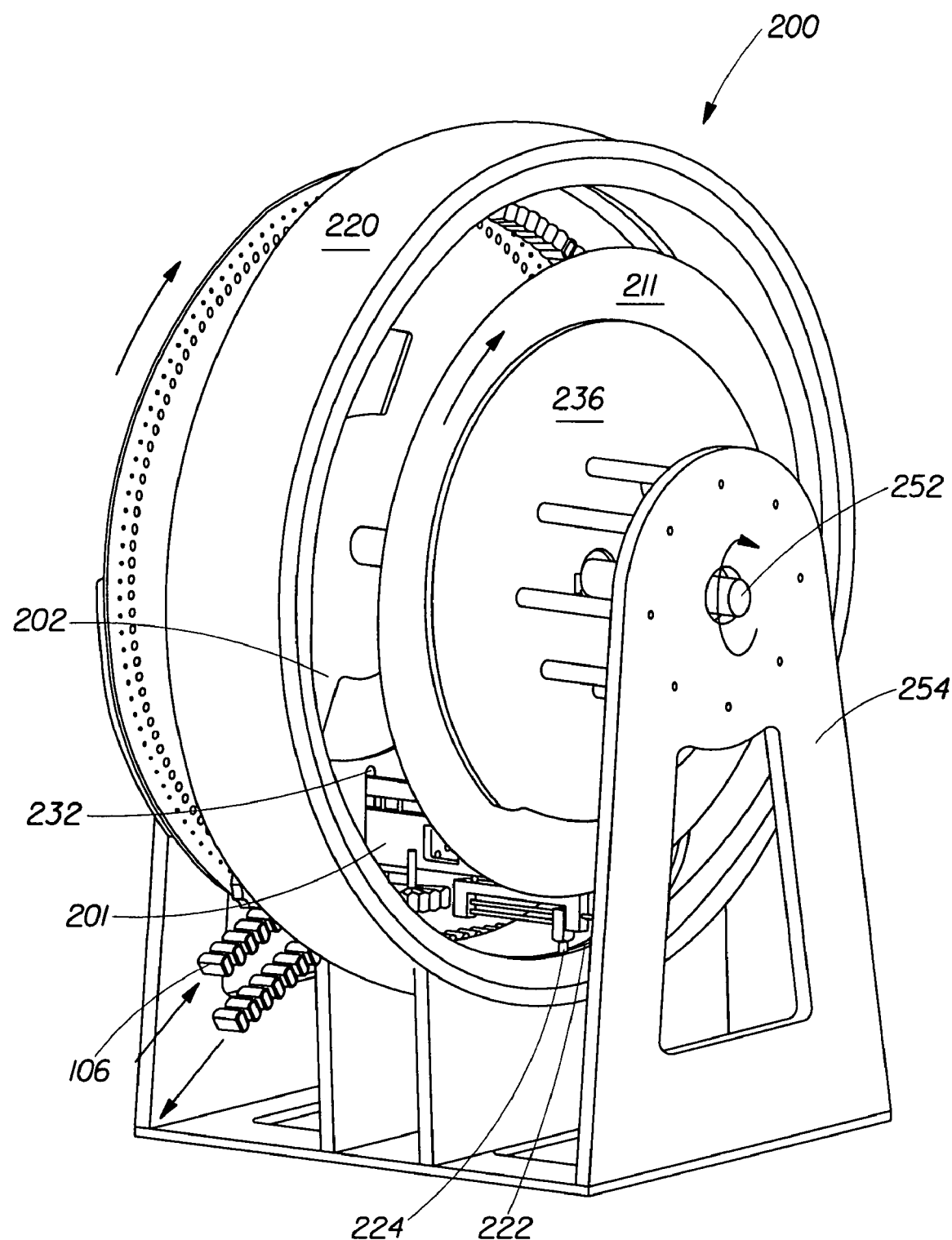
FIG. 25 is a simplified perspective view of the rotary apparatus of FIG. 24, viewing from the opposite direction than that in FIG. 24.

FIG. 25 is a is a simplified perspective view of the rotary apparatus 200 of FIG. 24, viewing from the opposite direction than that in FIG. 24.

Figure 26:
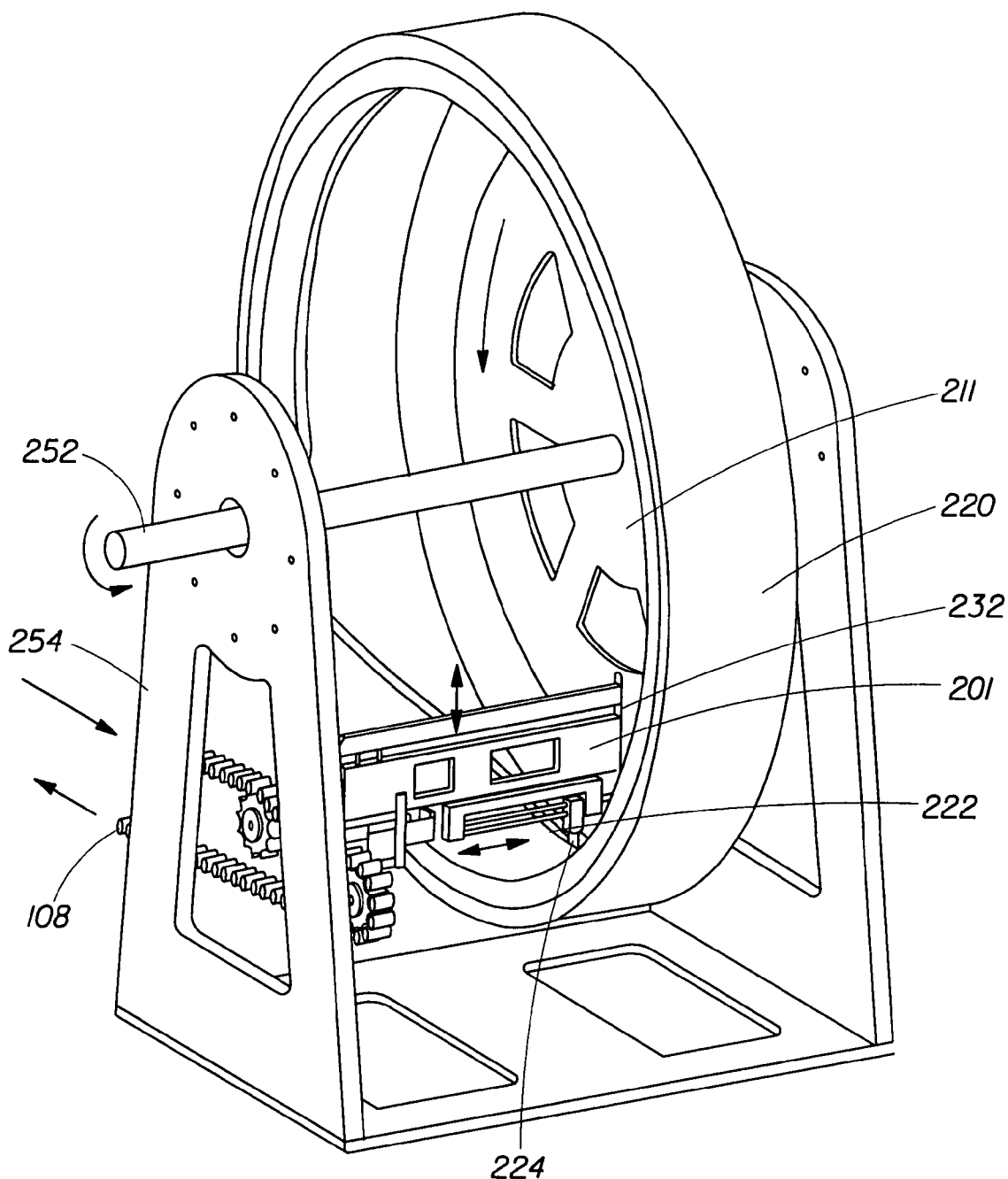
FIG. 26 is a simplified perspective view of one of the multiple tooling stations, a cylindrical cam, and a tampon discharge carrier of the rotary apparatus of FIG. 24, without a drum side plate, a mold-closing cam, and a pledget infeed carrier.

FIG. 26 is a simplified perspective view of one of the multiple tooling stations 201, a cylindrical cam 220, and a tampon discharge carrier 108 of the rotary apparatus of FIG. 24, without a drum side plate 202, a mold-closing cam 234, and a pledget infeed carrier 106.

Figure 27:
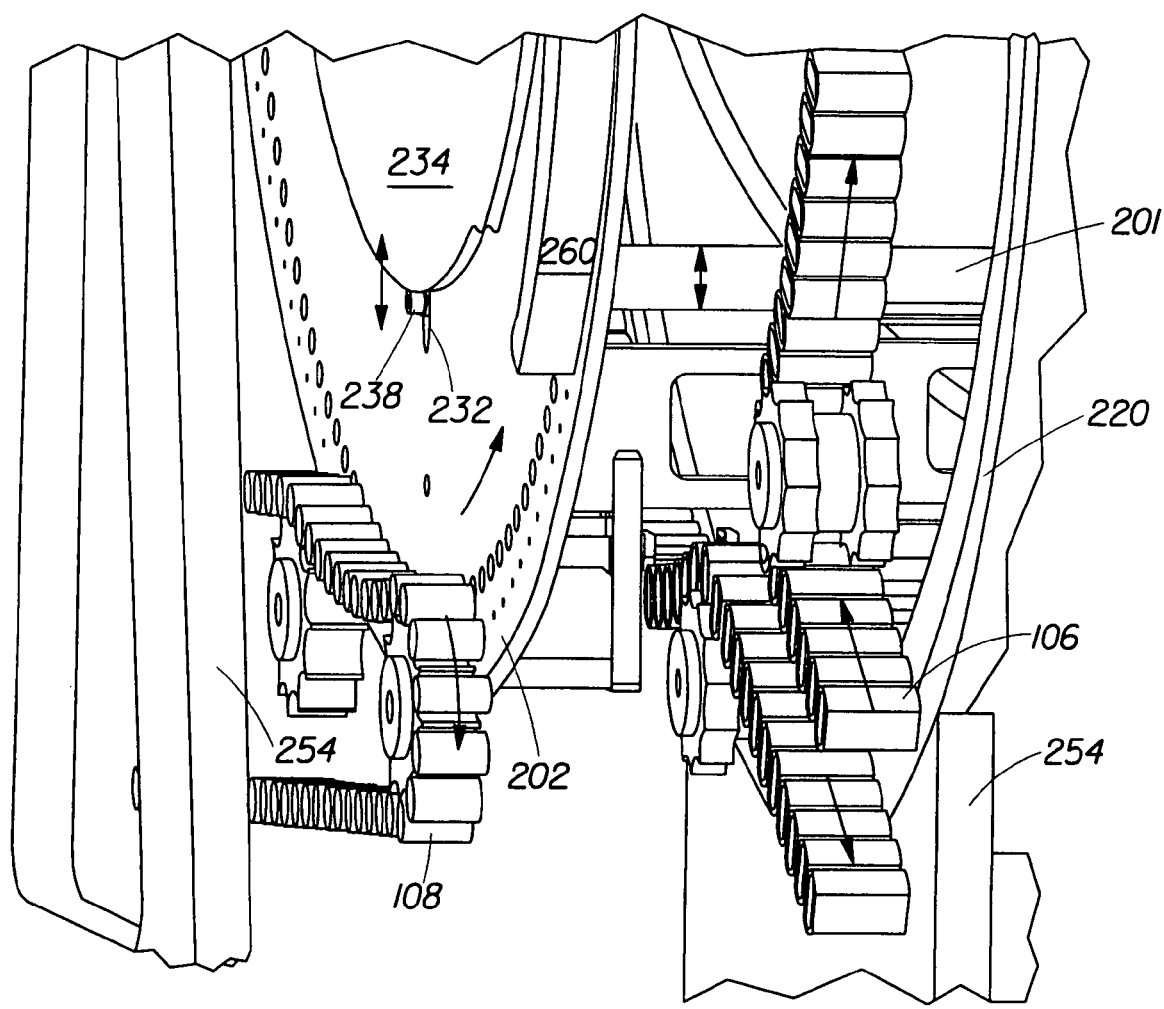
FIG. 27 is a simplified, magnified perspective view of the pledget infeed carrier and the tampon discharge carrier of the rotary apparatus of FIG. 24.

FIG. 27 is a simplified, magnified perspective view of the pledget infeed carrier 106 and the tampon discharge carrier 108 of the rotary apparatus of FIG. 24.

Figure 28:
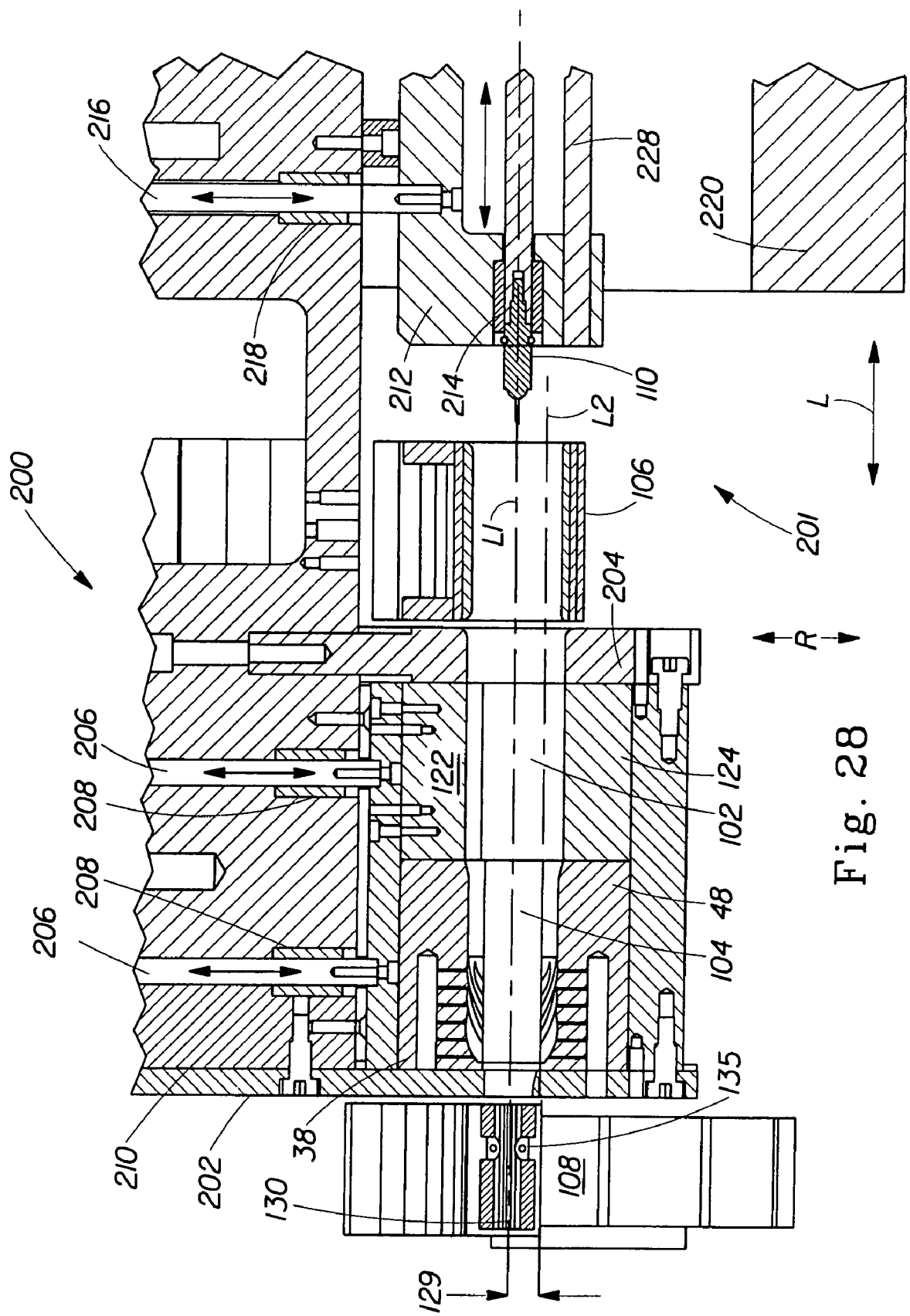
FIG. 28 is a simplified cross-sectional view of the rotary apparatus of FIG. 23 taken along line 28-28 crossing a tooling station.

FIG. 28 is a simplified cross-sectional view of the rotary apparatus 200 of FIG. 23 taken along line 28-28 crossing the tooling station 201.

Each of the tooling stations 201 includes a pair of molds (the split compression mold 102 and the split stabilization mold 104) and a transfer member 110. The split compression mold 102 includes a moving member 122 capable of moving in the radial direction R in relation to a fixed member 124 that is fixed. Similarly, the split stabilization mold 104 includes a moving member 38 capable of moving in the radial direction R in relation to a fixed member 48 that is also fixed.

Figure 29:
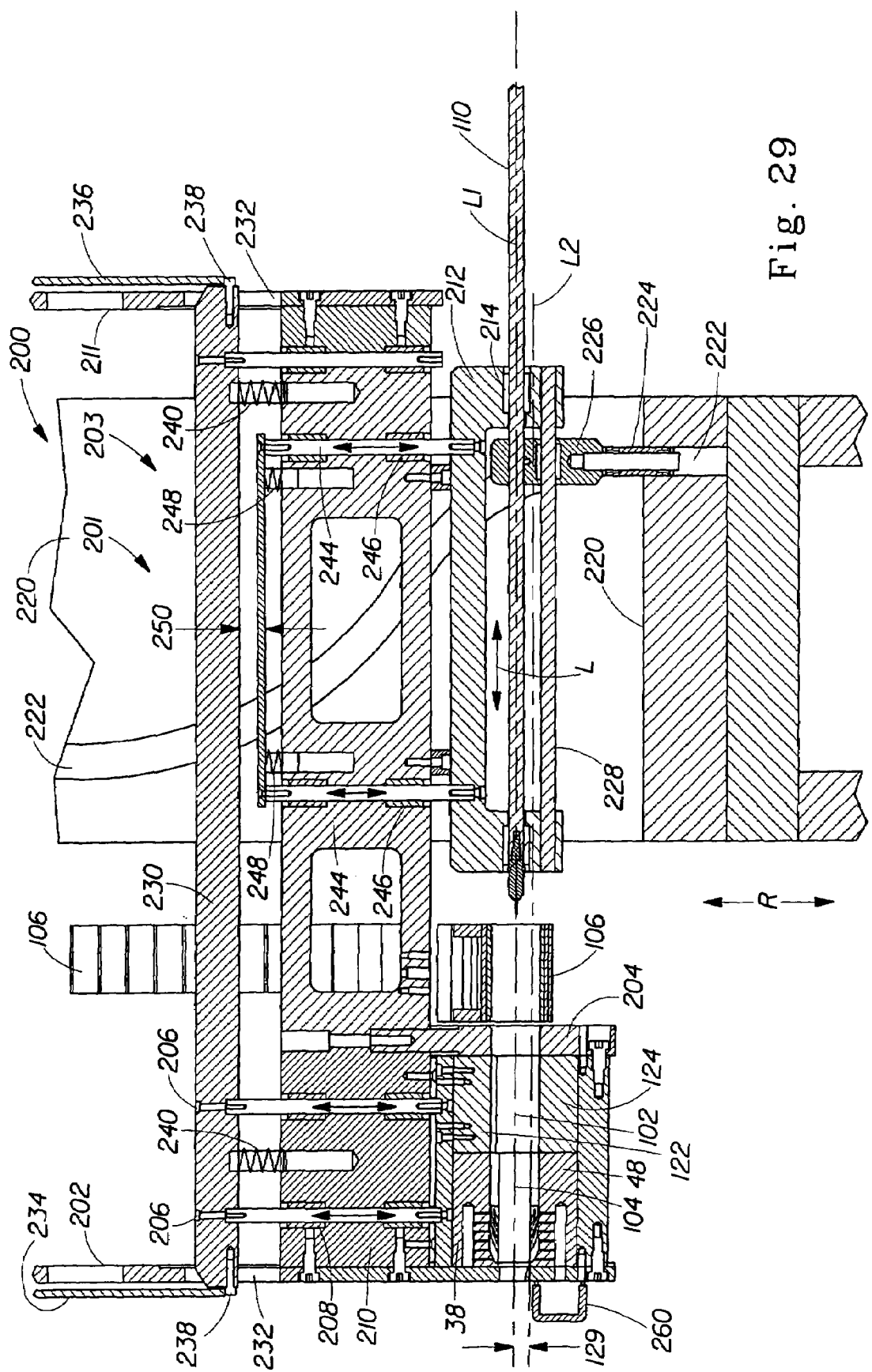
FIG. 29 is simplified cross-sectional view of the rotary apparatus of FIG. 23 taken along line 29-29 crossing a gas manifold for supplying a gas into the stabilizing mold.

FIG. 29 is simplified cross-sectional view of the rotary apparatus of FIG. 23 taken along line 29-29 crossing a gas manifold 260 for supplying a gas into the stabilizing mold 104.

Referring to both FIGS. 28 and 29, both fixed members 124 and 48 of the molds 102 and 104, respectively, are fixedly attached to a drum first side plate 202 and to a bracket 204 opposing the drum first side plate 202. However, both the moving members 122 and 38 of the molds 102 and 104, respectively, are capable to move in the radial direction R within the space created between the drum first side plate 202 and the bracket 204. The movement of the moving members 122 and 38 is guided by columns 206 capable of sliding in bushings 208 fixedly attached to a tooling frame 210 that is fixedly attached to the drum first side plate 202 and a drum second side plate 211 (shown in FIG. 29) opposing the drum first side plate 202. Both plates 202 and 211 are fixedly attached to a rotational shaft 252 (shown in FIG. 24) capable of rotating them. The columns 206 extend into a moving plate 230 (shown in FIG. 29) that can move in the radial direction R inside the opposing slots 232 (also shown in FIGS. 25 and 26) of the drum side plates 202 and 211. The radial movement of the moving plate 230 is provided by two opposing mold-closing cams 234 and 236 and two cam followers 238 fixedly attached to the moving plate 230. The cam followers 238 are spring-loaded against the mold-closing cams 234 and 236 by two opposing springs 240.

The transfer member 110 can move in the radial direction R by the action of the moving plate 230 pushing a plate 242 in the radial direction R. The plate 242 is guided by two columns 244 fixedly attached to the plate 242 and a transfer member bracket 212 containing the transfer member 110. Two columns 244 are sliding in bushings 246 fixedly attached to the tooling frame 210. The plate 242 is spring-loaded by springs 248 and spaced from the moving plate 230 in the radial direction R at a distance 250 providing a desired ratio (preferably 1:2) between the radial movement of the transfer member 110 and the radial movement of the both moving members 122 and 38 of the compression mold 102 and the stabilization mold 104, respectively.

It should be noted that rather than moving the transfer member 110 in the radial direction R, the fixed members 124 and 48 of the molds 102 and 104, respectively, can be movable to move in the radial direction R.

The transfer member 110 can also move in the longitudinal direction L inside the bushings 214 fixedly attached to the bracket 212. The longitudinal movement of the transfer member 110 is provided by the combination of a cylindrical cam 220 having an cam track 222, a cam follower 224 (shown in FIG. 29) moving inside the cam track 222, a bracket 226 fixedly attached to the cam follower 224 and to the transfer member 110, and a guide 228 disposed parallel to the transfer member 110.

FIG. 29 also shows a discharger carrier 108. In one embodiment of the present invention, the cavity 130 is defined preferably by a multiplicity of longitudinal flutes 133 to facilitate the dissipation of a gas forced into the cavity 130 during the stabilization process of the present invention. In addition, in one embodiment of the present invention (see FIG. 28), the tampon discharge carrier 108 can include preferably two opposing, spring-loaded plugs 135 penetrating into the cavity 130 for facilitating the retention of the tampon inside the cavity 130. The tampon discharge carrier 108 can be made from any material suitable for producing sanitary tampons.

Figure 30:
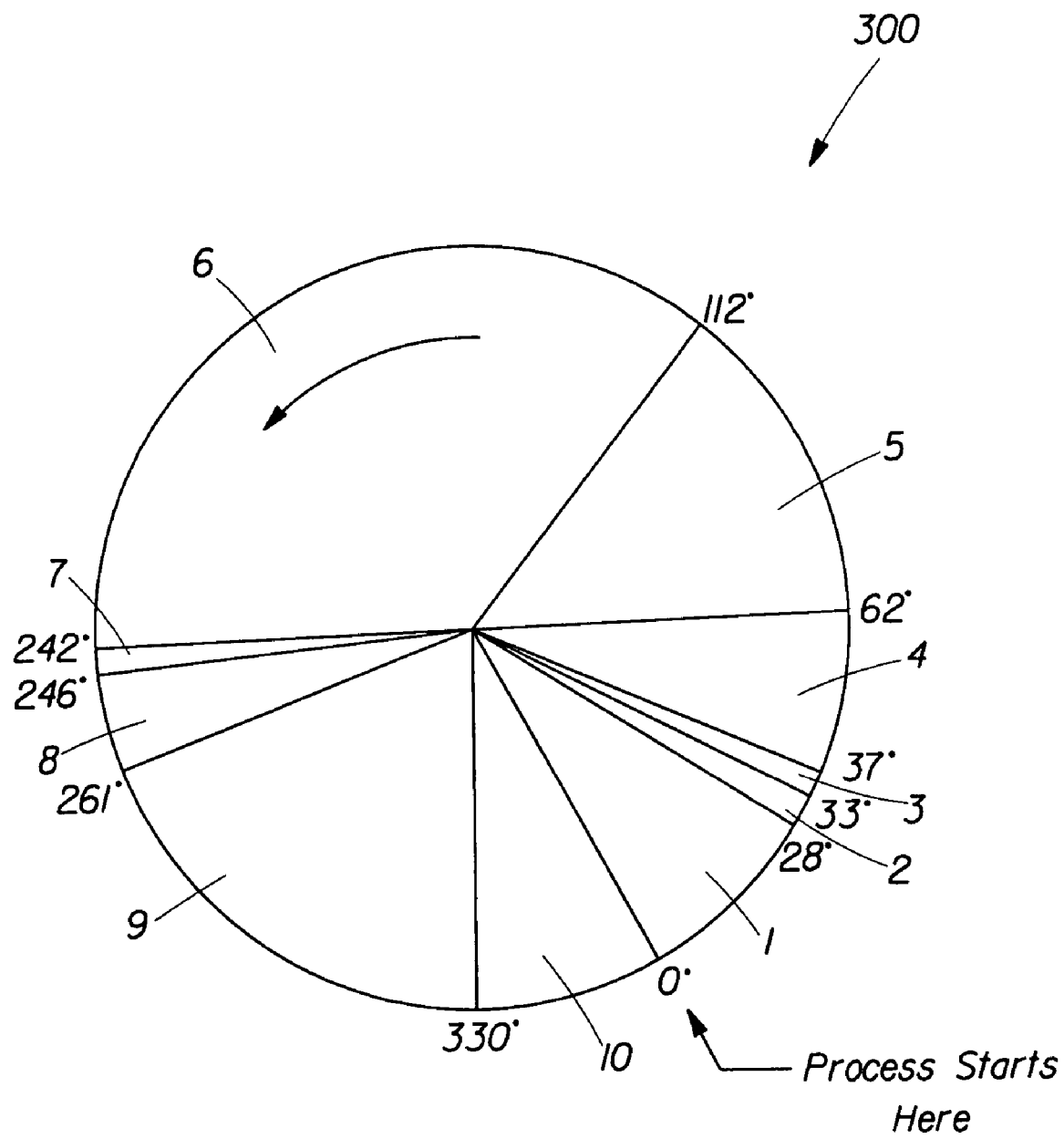
FIG. 30 is a circular time chart showing an exemplary sequence of process steps occurring in one embodiment of the present invention at certain degrees of rotation of a single tooling station during a full revolution thereof.

FIG. 30 is a time chart 300 showing an exemplary sequence of process steps occurring in one embodiment of the present invention at certain degrees of rotation of the tooling station 201 the during a full revolution thereof. Therefore, for other contemplated embodiments of the present invention, the sequence of process steps and the degrees of rotation, at which they occur, can vary.

The chart 300 shows the following process steps:

| Process Step No. | Process Step Name | Starting Degree of Rotation | FIG. No. Representing Process Step |
|---|---|---|---|
| 1 | Loading a pledget into a compression mold | 0 | FIG. 15 |
| 2 | Retracting a transfer member from the pledget | 28 | FIG. 16 |
| 3 | Compressing the pledget in the compression mold into a compressed tampon | 33 | FIG. 17 |
| 4 | Loading the compressed tampon into a stabilization mold | 37 | FIG. 18 |
| 5 | Injecting a gas into the stabilization mold | 62 | FIG. 19 |
| 6 | Holding the compressed tampon | 112 | |

-continued

| Process Step No. | Process Step Name | Starting Degree of Rotation | FIG. No. Representing Process Step |
|---|---|---|---|
| | in the stabilization mold to form a stabilized tampon | | |
| 7 | Opening the molds | 242 | FIG. 20 |
| 8 | Loading the stabilized tampon into a tampon discharge carrier | 246 | FIG. 21 |
| 9 | Retracting the transfer member | 261 | FIG. 22 |
| 10 | Exiting the tampon discharge carrier and providing a pledget infeed carrier containing a pledget | 330 | |

A Compressed, Gas-Stabilized Tampon

The compressed, gas-stabilized tampon 132 of the present invention can have any suitable shape including, but not limited to, cylindrical, rectangular, triangular, trapezoidal, semi-circular, hourglass, serpentine, or any combination thereof.

The tampon 132 can be compressed from any suitable pre-compressed shape pledget 112, including, but not limited to, generally chevron shape, a rectangular shape, a trapezoidal shape, a triangular shape, a semi-circular shape, an "H" shape, a "bow-tie" shape or any combination thereof.

The pledget 112 can be constructed from a wide variety of liquid-absorbing materials commonly used in absorbent articles. The absorbent material of the pledget 112 can be surrounded with any suitable liquid-permeable overwrap material, if desired. Further, the pledget 112 can be a laminar structure comprised of integral or discrete layers comprising same or different materials, including uniform or non-uniform blend of materials. Further, the pledget 132 can vary in absorbent material density along the axial extent of the pledget 112.

The tampon 132, as shown in FIG. 22, can include a secondary absorbent member 114 and a withdrawal cord 115. Both the secondary absorbent member 114 and the withdrawal cord 115 can be constructed from any suitable materials commonly used in production of disposable articles.

Figure 31:
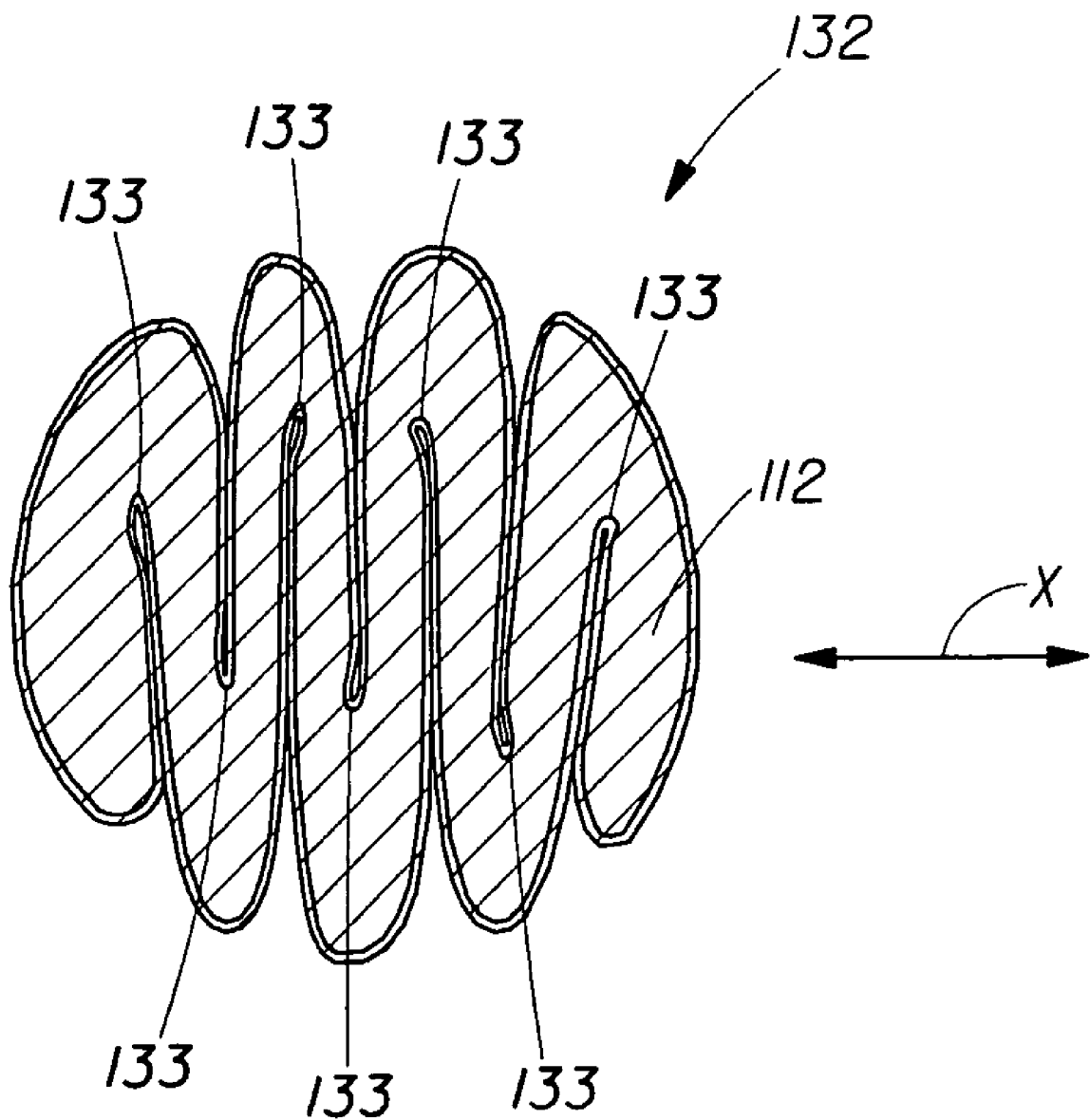
FIG. 31 is a cross-sectional view of one exemplary embodiment of the compressed, gas-stabilized tampon of the present invention having multiple folds.

The tampon 132 can have a folded construction, wherein the pledget 112 has a multiplicity of longitudinal, generally parallel folds which can be provided prior to and/or as a result of the compression step of the method of the present invention. An exemplary embodiment of the gas-stabilized tampon 132 is shown in FIG. 31 illustrating a cross sectional view taken generally perpendicular to the longitudinal direction of the tampon 132. The illustrated embodiment has seven folds 133 extending generally parallel in the longitudinal direction of the tampon 132. It should be noted that other embodiments of the gas-stabilized tampon 132 of the present invention can have any suitable number of folds. For example, the number of folds can range from 3 to 20 or to any suitable large number. Also, for example, the number of folds can be from 5 to 11 or from 7 to 8. In addition, the folds can be of any suitable size including so small that they are not apparent to the naked eye. Also, the folds can be substantially uniform along the entire pledget 112 or not uniform.

The multiple-fold configuration of the gas-stabilized tampon 132 provides for improved expansion characteristics of the tampon 132 inside a vaginal channel during use. The improved expansion characteristics of the tampon 132 include greater expansion in the direction X shown in FIG. 31, wherein the direction X generally coincides with the direction of the compression force previously applied to the tampon 132 during the production of the folds 133. Generally, greater number of folds 133 can provide greater expansion in the X direction. As a benefit, such X directional expansion of the tampon 132 can provide improved fit inside a vagina (which is typically generally flat) thus reducing the potential for leakage, especially in the early stages of the tampon use before it becomes sufficiently expanded. Another benefit resulting from the X directional expansion of the tampon 132 can be the improved comfort to the user.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for producing a stabilized compressed tampon comprising the steps of:
   a. providing a tampon pledget;
   b. providing a mold, said mold containing a plurality of pores;
   c. compressing said tampon pledget in said mold to form a compressed tampon pledget; and
   d. stabilizing said compressed tampon pledget by forcing a gas through said pores while said compressed tampon is maintained in compression by said mold.

2. The process of claim 1 wherein the amount of said pores per unit area varies along the length of said mold.

3. The process of claim 1 wherein said pores are located on said mold radially, axially or combinations thereof.

4. The process of claim 1 wherein said mold is a split cavity mold comprising an inner cavity defined by an inner surface formed from a first split cavity mold member and a second split cavity mold member wherein said first split cavity mold member has a first and second end that corresponds to a first and second end of said second split cavity mold member.

5. The process of claim 4 wherein the amount of said pores per unit area in said inner surface increases along the length of the split cavity mold in the direction of the first end of the first and second split cavity mold members.

6. The process of claim 4 wherein the amount of said pores per unit area in said inner surface increases along the length of the split cavity mold in the direction of the second end of the first and second split cavity mold members.

7. The process of claim 1 wherein said mold is a unitary mold comprising an inner cavity defined by an inner surface, an open proximal end and a closed distal end.

8. The process of claim 7 wherein the amount of said pores per unit area in said inner surface increases along the length of the unitary mold in the direction of the proximal end of the inner cavity.

9. The process of claim 7 wherein the amount of said pores per unit area in said inner surface increases along the length of the unitary mold in the direction of the distal end of the inner cavity.

10. A process for producing a stabilized compressed tampon comprising the steps of:
    a. providing a tampon pledget;
    b. providing a mold, said mold containing a plurality of pores; wherein said pores vary in size from about macroscopic to about submicroscopic
    c. compressing said tampon pledget into said mold to form a compressed tampon pledget; and
    d. stabilizing said compressed tampon pledget by forcing a gas through said pores while said compressed tampon pledget is maintained in compression by said mold.

11. The process of claim 10 wherein the diameter of said pores ranges from about 0.2 mm to about 1.5 mm.

12. The process of claim 10 wherein the size of said pores varies along the length of said mold.

13. The process of claim 10 wherein said pores are located on said mold radially, axially or combinations thereof.

14. The process of claim 10 wherein said mold is a split cavity mold comprising an inner cavity defined by an inner surface formed from a first split cavity mold member and a second split cavity mold member wherein said first split cavity mold member has a first and second end that corresponds to a first and second end of said second split cavity mold member.

15. The process of claim 14 wherein the size of said pores in said inner surface increases along the length of the split cavity mold in the direction of the first end of the first and second split cavity mold members.

16. The process of claim 14 wherein the size of said pores in said inner surface increases along the length of the split cavity mold in the direction of the second end of the first and second split cavity mold members.

17. The process of claim 10 wherein said mold is a unitary mold comprising an inner cavity defined by an inner surface, an open proximal end and a closed distal end.

18. The process of claim 17 wherein the size of said pores in said inner surface increases along the length of the unitary mold in the direction of the proximal end of the inner cavity.

* * * * *

UNITED STATES PATENT AND TRADEMARK OFFICE
CERTIFICATE OF CORRECTION

PATENT NO. : 7,472,463 B2
APPLICATION NO. : 11/809691
DATED : January 6, 2009
INVENTOR(S) : Gilbert et al.

It is certified that error appears in the above-identified patent and that said Letters Patent is hereby corrected as shown below:

<u>Column 15</u>

Line 52, delete "30,".

<u>Column 17</u>

Line 60, delete "Fig. 1." and insert --Fig. 11.--.

Signed and Sealed this

Twenty-fifth Day of August, 2009

David J. Kappos
*Director of the United States Patent and Trademark Office*